(12) United States Patent
Numata et al.

(10) Patent No.: US 10,179,779 B2
(45) Date of Patent: Jan. 15, 2019

(54) POLYMORPH FORMS

(71) Applicant: RaQualia Pharma Inc., Aichi (JP)

(72) Inventors: Toyoharu Numata, Aichi (JP);
Hideyuki Aoyama, Aichi (JP); Kaori Muraji, Aichi (JP)

(73) Assignee: RaQualia Pharma Inc., Aichi (JP)

( * ) Notice: Subject to any disclaimer, the term of this patent is extended or adjusted under 35 U.S.C. 154(b) by 0 days.

(21) Appl. No.: 14/442,860

(22) PCT Filed: Nov. 21, 2013

(86) PCT No.: PCT/JP2013/006853
§ 371 (c)(1),
(2) Date: May 14, 2015

(87) PCT Pub. No.: WO2014/080633
PCT Pub. Date: May 30, 2014

(65) Prior Publication Data
US 2015/0322055 A1   Nov. 12, 2015

Related U.S. Application Data

(60) Provisional application No. 61/729,174, filed on Nov. 21, 2012.

(51) Int. Cl.
*C07D 413/14* (2006.01)

(52) U.S. Cl.
CPC ........ *C07D 413/14* (2013.01); *C07B 2200/13* (2013.01)

(58) Field of Classification Search
CPC .................................................. C07D 413/14
USPC ........................................ 514/321; 546/198
See application file for complete search history.

(56) References Cited

U.S. PATENT DOCUMENTS

| 5,538,984 | A | 7/1996 | Villalobos et al. | |
|---|---|---|---|---|
| 5,750,542 | A | 5/1998 | Villalobos et al. | |
| 6,106,864 | A | 8/2000 | Dolan et al. | 424/488 |
| 6,326,382 | B1 | 12/2001 | Villalobos et al. | |
| 2002/0028834 | A1 | 3/2002 | Villalobos et al. | |

FOREIGN PATENT DOCUMENTS

| RU | 2 119 920 | 10/1998 |
|---|---|---|
| WO | 91/11172 | 8/1991 |
| WO | 94/02518 | 2/1994 |
| WO | 98/55148 | 12/1998 |
| WO | 00/35298 | 6/2000 |
| WO | 2006/090224 | 8/2006 |
| WO | 2012/157288 | 11/2012 |

OTHER PUBLICATIONS

Gavezzott "A solid state chemists' . . . " J. Pharm. Sci. 96(9) p. 2232-2241 (2007).*
Guidance for industry ANDAs, FDA p. 1-13 (2007).*
Obaidat et al. "Determination of factors. . . " Drug. Develop. Ind. Pharm. 36(5) 570-580 (2010).*
US Pharmacopeia p. 1843-1844 (1995).*
UserCom "Interpreting DSC . . . " p. 1-4 (2000).*
Zell et. al. "Investigation of Polymorphism in Aspartame and Neotame Using Solid-State NMR Spectroscopy." Tetrahedron 2000, 56, 6603-6616.*
Bernstein, Joel "Polymorphism in Molecular Crystals" 2002, Oxford: New York, pp. 115, 117.*
Cabri et. al. "Polymorphisms and Patent, Market, and Legal Battles: Cefdinir Case Study" Organic Process Research & Development 2007, 11, 64-72.*
Bernstein, Joel "Polymorphism in Molecular Crystals" 2002, Oxford: New York, p. 46.*
Braga "Crystal Polymorphism and Multiple Crystal Forms" Chapter in Structure and Bonding Springer-Verlag Berlin Heidelberg 2009.*
Healy "Pharmaceutical solvates, hydrates and amorphous forms: A special emphasis on cocrystals" Advanced Drug Delivery Reviews (2017) in press, pp. 1-22.*
Bernstein " . . . And Another Comment on Pseudopolymorphism" Crystal Growth & Design, vol. 5, No. 5, 2005 1661-1662, Emphasis added.].*
Draft chapter for The International Pharmacopoeia 5 (Jul. 2017) on Polymorphism.*
International Search Report dated Dec. 17, 2013 in International (PCT) Application No. PCT/JP2013/006853.
Written Opinion of the International Searching Authority dated Dec. 17, 2013 in International (PCT) Application No. PCT/JP2013/006853.
Bockaert et al., "The 5-$HT_4$ receptor: a place in the sun", TiPS Review, vol. 13, Apr. 1992, pp. 141-145.
Ford et al., "The 5-$HT_4$ Receptor", Medicinal Research Reviews, vol. 13, No. 6, 1993, pp. 633-662.
Gullikson et al., "Gastrointestinal Motility Responses to the S and R Enantiomers of Zacopride, a 5-HT4 Agonist and 5-HT3 Antagonist", Drug Development Research, vol. 26, 1992, pp. 405-417.
Eglen et al., "Central 5-$HT_4$ receptors", TiPS Review, vol. 16, Nov. 1995, pp. 391-398.
Bockaert et al., "5-$HT_4$ receptors Potential Therapeutic Implications in Neurology and Psychiatry", CNS Drugs, vol. 1 (1), 1994, pp. 6-15.
Romanelli et al., "Synthesis and Biological Activity of a Series of Aryl Tropanyl Esters and Amides Chemically Related to 1H-Indole-3-carboxylic Acid endo 8-Methyl-8-azabicyclo [3.2.1]oct-3-yl Ester", Arzheim Forsch./Drug Research, vol. 43(II), No. 8, 1993, pp. 913-918.
Kaumann et al., "A 5-$HT_4$-like receptor in human right atrium", Naunyn-Schmiedeberg's Arch Pharmacol, vol. 344, 1991, pp. 150-159.

(Continued)

*Primary Examiner* — David K O'Dell
(74) *Attorney, Agent, or Firm* — Wenderoth, Lind & Ponack, L.L.P.

(57) ABSTRACT

The present invention relates to novel crystal forms of 4-{[4-({[4-(2,2,2-trifluoroethoxy)-1,2-benzisoxazol-3-yl] oxy}methyl)piperidin-1-yl]methyl}-tetrahydro-2H-pyran-4-carboxylic acid. More particularly, the invention relates to polymorph forms of Polymorph Form I, Polymorph Form II, Polymorph Form III, Polymorph Form IV, Polymorph Form V, and Polymorph Form VI, and to processes for the preparation of, compositions containing and to uses of, such polymorph forms.

18 Claims, 6 Drawing Sheets

(56) References Cited

OTHER PUBLICATIONS

Remington's Pharmaceutical Sciences (The Science and Practice of Pharmacy), 19th edition, (Mack Publishing Company, 1995).
Liang et al., "Fast-dissolving intraoral drug delivery systems", Expert Opin. Ther. Patents, vol. 11(6), 2001, pp. 981-986.
Lieberman et al., "Pharmaceutical Dosage Forms", Tablets, vol. 1, 1980.
Verma et al., "Current Status of Drug Delivery Technologies and Future Directions", Pharmaceutical Technology On-Line, vol. 25 (2), 2001, pp. 1-14.
Finnin et al., "Transdermal Penetration Enhancers: Applications, Limitations, and Potential", Journal of Pharmaceutical Sciences, vol. 88, No. 10, Oct. 1999, pp. 955-958.
Evrard et al., "Cyclodextrins as a potential carrier in drug nebulization", Journal of Controlled Release, vol. 96, 2004, pp. 403-410.
Bryn et al., "Solid-State Chemistry of Drugs", SSCI, Inc., Second edition, 1999, pp. 3-43 and 461-503.
Office Action dated Oct. 16, 2017 in Russian Application No. 2015123687, with English translation.

\* cited by examiner

{Fig. 1}
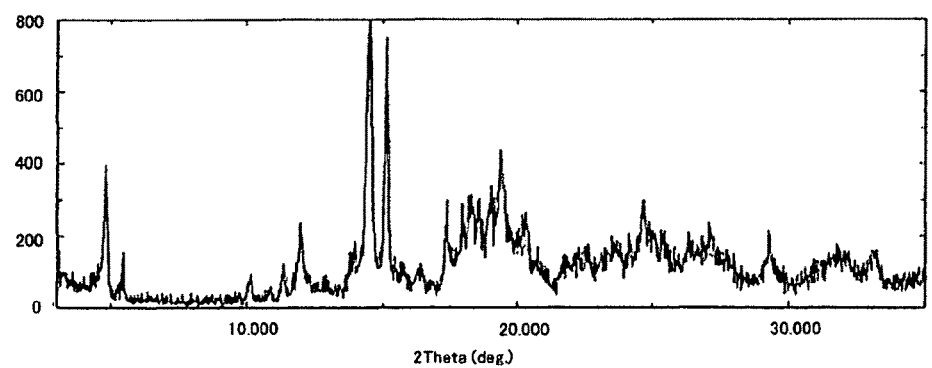
{Fig. 2}
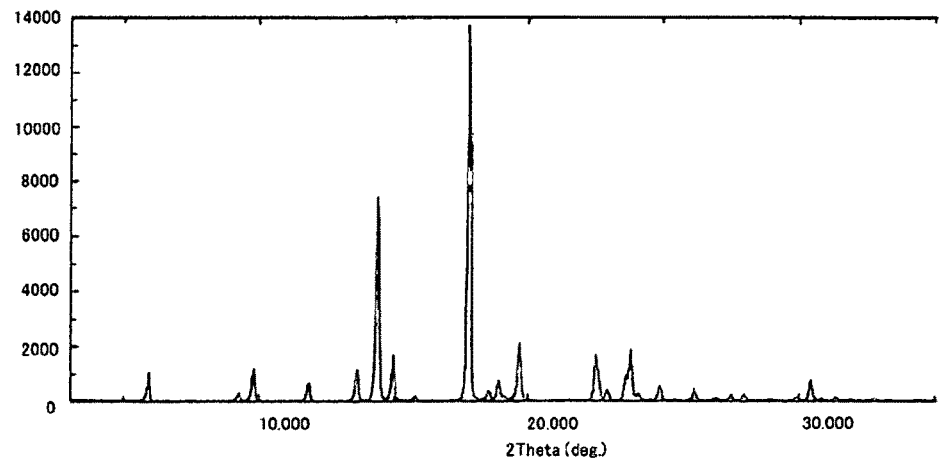

{Fig. 3}
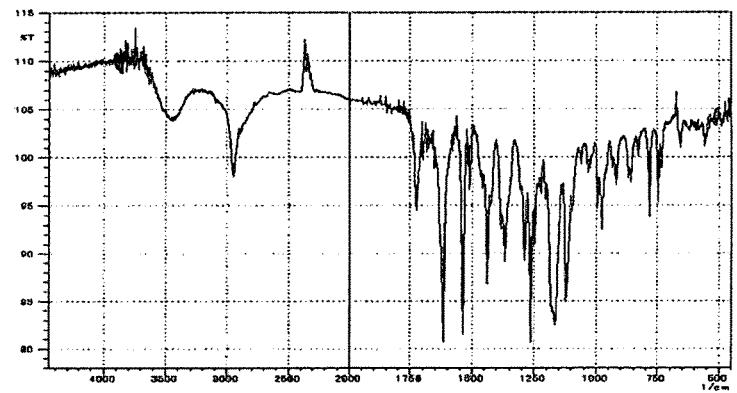
{Fig. 4}
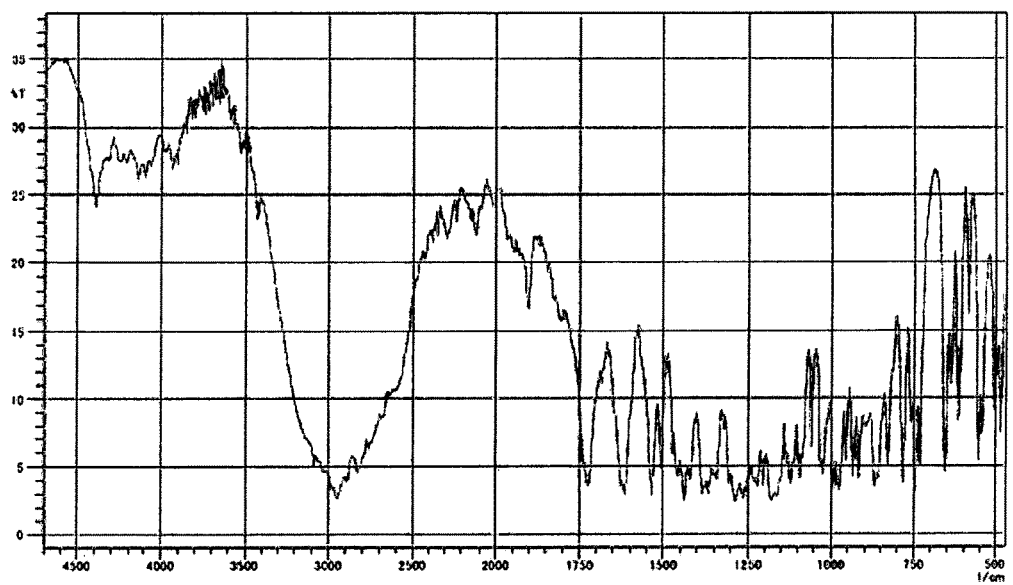

{Fig. 5}
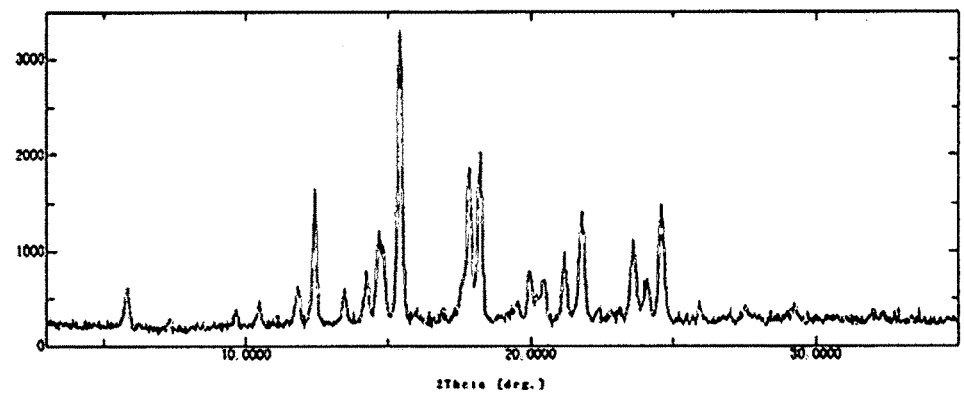
{Fig. 6}
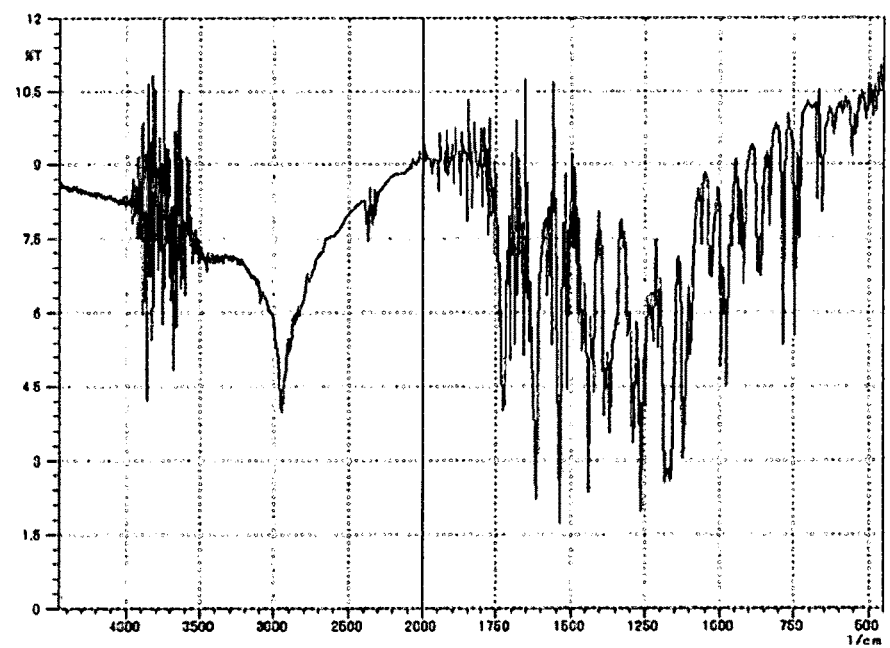

{Fig. 7}
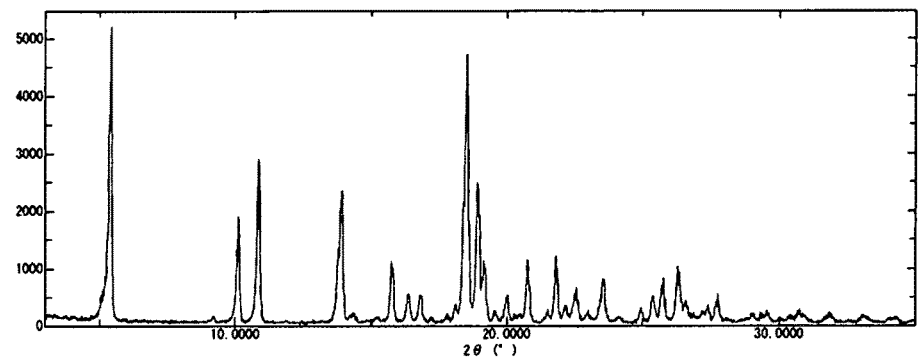
{Fig. 8}
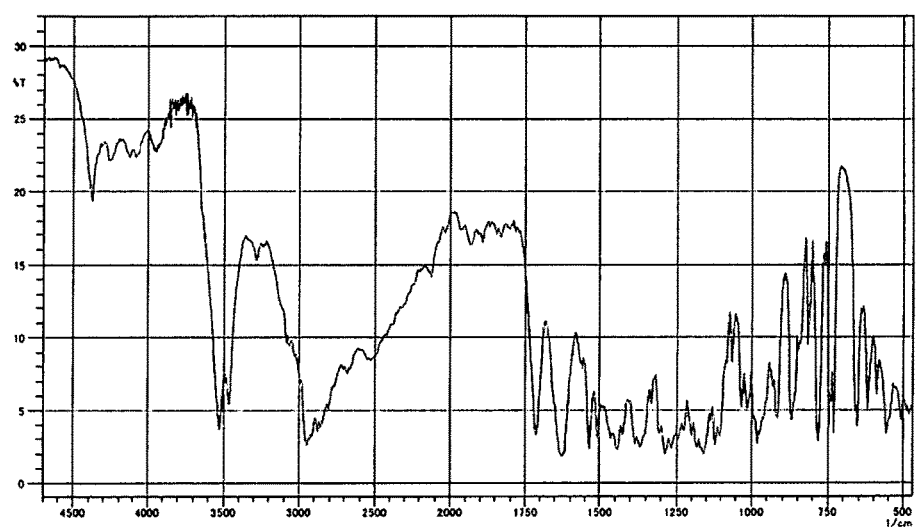
{Fig. 9}
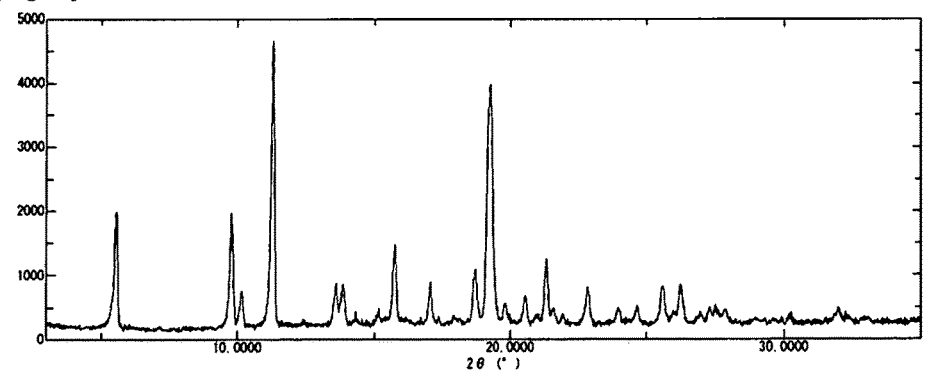

{Fig. 10}
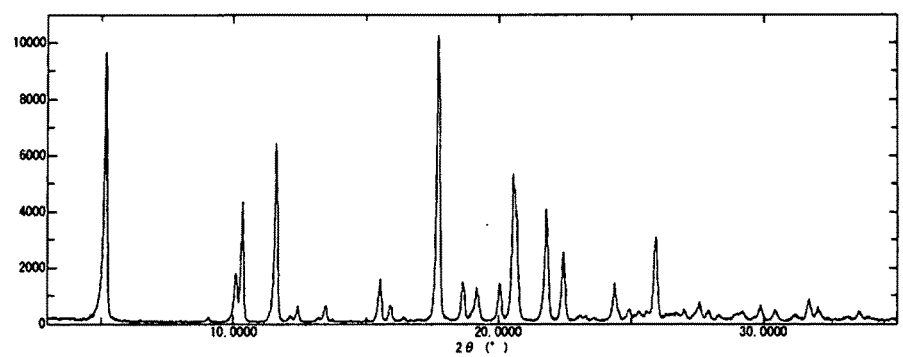
{Fig. 11}
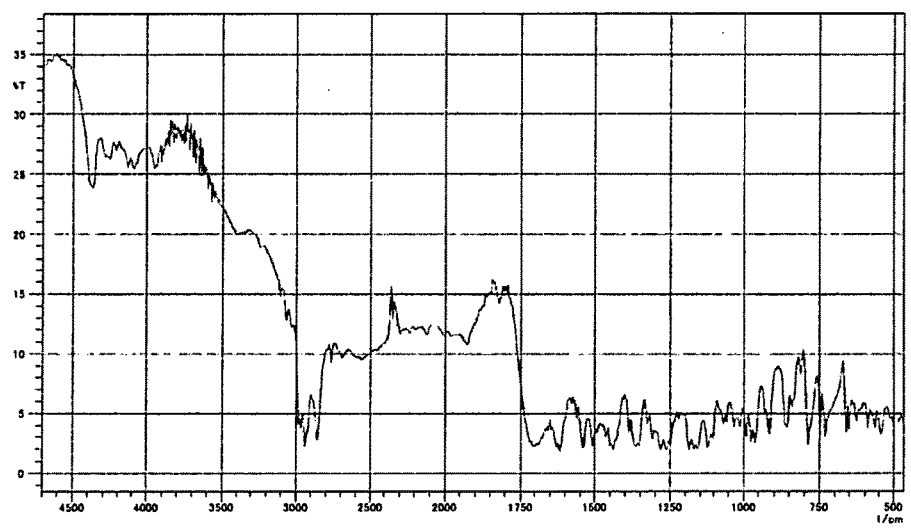
{Fig. 12}
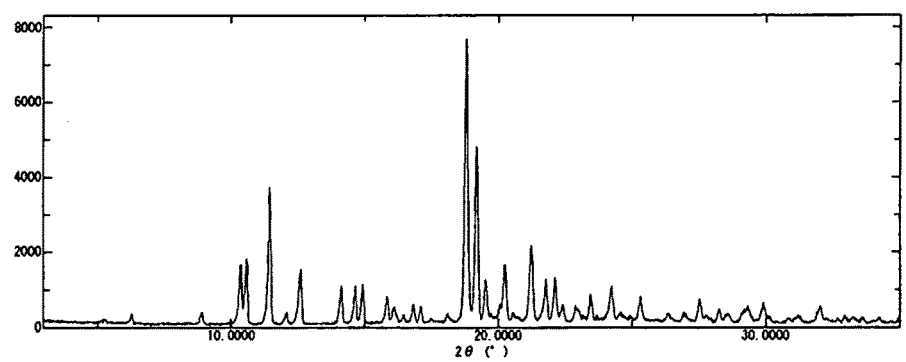

{Fig. 13}
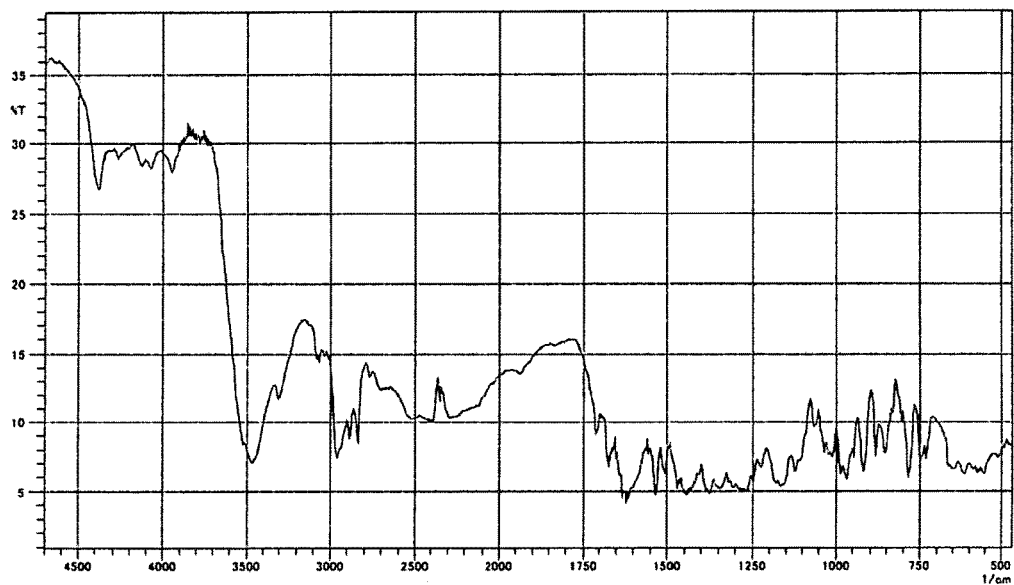
{Fig. 14}
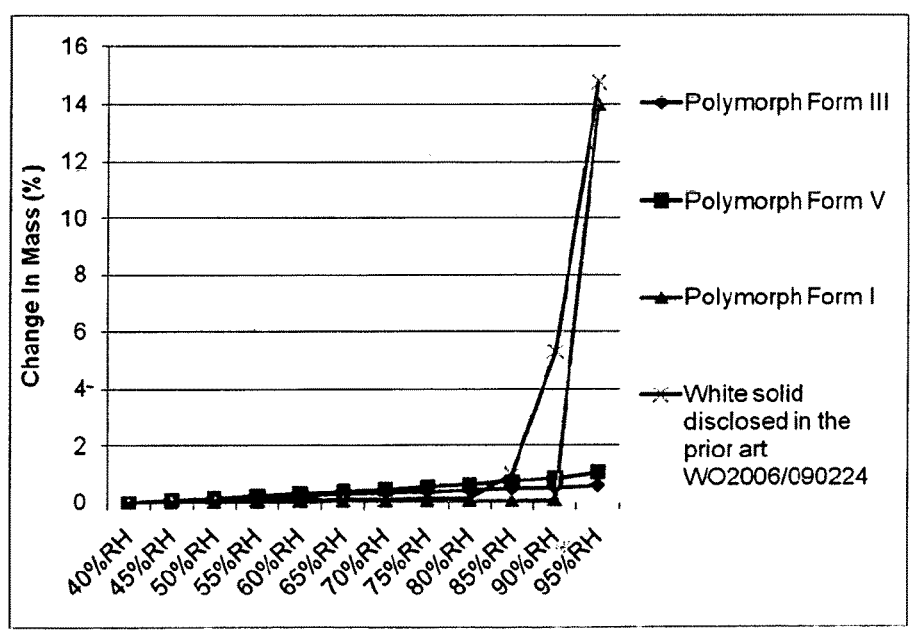

POLYMORPH FORMS

TECHNICAL FIELD

The present invention relates to novel crystal forms of 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid.

More particularly, the invention relates to polymorph forms (Polymorph Form I, Polymorph Form II, Polymorph Form III, Polymorph Form IV, Polymorph Form V and Polymorph Form VI), and to processes for the preparation of, compositions containing and to uses of, such polymorph forms.

BACKGROUND ART

4-{[4-({[4-(2,2,2-Trifluoroethoxy)-1,2-benzisoxazol-3-yl]oxy}methyl)piperidin-1-yl]methyl}-tetrahydro-2H-pyran-4-carboxylic acid is disclosed in PL1 as a 5-HT4 receptor agonist, which is useful in the treatment or alleviation of disease conditions mediated by 5-HT4 receptor activity; in particular 5-HT4 receptor antagonistic activity, such as gastroesophageal reflux disease (GERD), gastrointestinal disease, gastric motility disorder, non-ulcer dyspepsia, functional dyspepsia (FD), irritable bowel syndrome (IBS), constipation, dyspepsia, esophagitis, gastroesophageal disease, gastritis, nausea, central nervous system disease, Alzheimer's disease, cognitive disorder, emesis, migraine, neurological disease, pain, cardiovascular disorders, cardiac failure, heart arrhythmia, diabetes, and apnea syndrome (See NPL 1 to 13 and PL 2 to 7).

Simply an white solid has been produced in the previously known methods of preparing 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid, described in PL 1. Therefore, neither a crystal nor mixture of crystal forms have been known to the public.

CITATION LIST

Patent Literature

{PL 1} WO2006/090224.
{PL 2} U.S. Pat. No. 6,106,864.
{PL 3} WO 00/35298.
{PL 4} WO 91/11172.
{PL 5} WO 94/02518.
{PL 6} WO 98/55148.
{PL 7} PCT/JP2012/003288.

Non Patent Literature

{NPL 1} Bockaert J. et al., TiPs 13; 141-45, 1992.
{NPL 2} Ford A. P et al., Med. Res. Rev. 13: 633-62, 1993.
{NPL 3} Gullikson G. W. et al., Drug Dev. Res. 26; 405-17, 1992.
{NPL 4} Richard M. Eglen et al., TiPs 16; 391-98, 1995.
{NPL 5} Bockaert J. et al., CNS Drugs 1; 6-15, 1994.
{NPL 6} Romanelli M. N. et al., Arzheim Forsch./Drug Res., 43; 913-18, 1993.
{NPL 7} Kaumann A. J. et al., Naunyn-Schmiedebergs Arch Pharmacol., 344; 150-59, 1991.
{NPL 8} Remington's Pharmaceutical Sciences, 19th Edition (Mack Publishing Company, 1995).
{NPL 9} Expert Opinion in Therapeutic Patents, H (6), 981-986, by Liang and Chen (2001).
{NPL 10} Tablets, Vol. 1, by H. Lieberman and L. Lachman (Marcel Dekker, New York, 1980).
{NPL 11} Pharmaceutical Technology On-line, 25(2), 1-14, by Verma et al. (2001).
{NPL 12} J Pharm Sci, 88 (10), 955-958, by Finnin and Morgan (October 1999).
{NPL 13} Evrard, B., et al., Journal of Controlled Release 96 (3), pp. 403-410, 2004.
{NPL 14} Byrn S. R. et al., Solid-State Chemistry of Drugs 2nd ed., pp 3-43 and 461-503, 1999, SSCI, Inc.

SUMMARY OF INVENTION

Technical Problem

As well-known by skilled in the art, it has been a desirable goal to find or prepare a crystalline or crystalline form in drug development from the various viewpoints including formulation and manufacturing of the drug (See Byrn S. R. et al., Solid-State Chemistry of Drugs 2nd ed., pp 3-43 and 461-503, 1999, SSCI, Inc.).

According to the line, great efforts have been made to find or prepare a crystalline or crystalline form of 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid since the said compound was disclosed in 2006 (WO2006/090224) by Pfizer Inc. For instance, esters such as ethyl acetate, alcohols such as methanol, ethanol and isopropyl alcohol, nitriles such as acetonitrile, ethers such as diethyl ether and MTBE (methyl t-butyl ether), ketones such as acetone and methyl ethyl ketone, halogenated hydrocarbons such as dichloromethane and chloroform were used as recrystallization solvents, but all of them resulted in failure.

In spite of such great efforts, no pharmaceutically suitable crystalline forms of the said compound have been identified yet.

As mentioned before, when ethyl acetate was used as a recrystallization solvent in a usual manner conducted by those skilled in the art, only unsuccessful results have been obtained. After an exhaustive and careful study, the inventors of the present invention have managed to find out a very special and unique condition of preparing the crystalline form using ethyl acetate, which can provide the long-awaited crystalline form (Polymorph Form I) of the said compound.

As disclosed in the working example of the present invention, a white solid of the said compound was suspended in ethyl acetate for 1 day at 40° C. and 5 days at room temperature (usually 15 to 35° C.) to afford to Polymorph Form I. Those skilled in the art have never thought of such crystallization condition.

Polymorph Form II has been obtained from the Polymorph Form I obtained in the special condition mentioned above. Polymorph Form I transforms to Polymorph Form II at 110° C. or higher temperature, but resulting Polymorph Form II converts to Polymorph Form I under measurement conditions such as nitrogen flow when cooling Polymorph Form II to room temperature. The inventors of the present invention also discovered a condition of obtaining Polymorph Form II at room temperature in the range of from 15 to 35° C.

In addition, once the seed of the crystalline form is obtained, the same crystalline form can generally be easily obtained in a small scale synthesis. On large scale synthesis, temperature control is essential for preparing a pharmaceutically suitable crystalline form.

According to the line, Polymorph Form I and Polymorph Form II was filed in the patent application as PCT/JP2012/003288 by the same applicant as the present patent application, which has never been laid open to the public.

Polymorph Form III has been obtained from Polymorph Form I in the following condition. Polymorph Form I transforms to Polymorph Form III under a high relative humidity condition, e.g. 70° C./75% RH. And even under 25° C./60% RH condition Polymorph Form I gradually transforms to Polymorph Form III.

In addition, Polymorph Form III has been also obtained under the condition of 3 to 5% (v/v) water in isopropyl alcohol or ethanol using the seed of Polymorph Form III.

Polymorph Form IV has been also obtained from the Polymorph Form III in the following condition. Polymorph Form III begins to transform to Polymorph Form IV at 90° C., and then completely transforms to Polymorph Form IV at 100° C.

Polymorph Form V has been also obtained from the Polymorph Form I in the following condition. Polymorph Form I transforms to Polymorph Form V under the suspension condition in water. In addition, Polymorph Form V has been also obtained under the condition of 10 to 50% (v/v) water in tetrahydrofuran.

Polymorph Form VI has been obtained from the Polymorph Form I in the following condition. Polymorph Form VI has been also obtained under the condition of 5 to 10% (v/v) water in acetone, 5 to 10% (v/v) water in acetonitrile or 5% (v/v) water in tetrahydrofuran.

Polymorph Form VI transforms to Polymorph Form III when it is dried.

It is an object of this invention to provide pharmaceutically suitable crystalline forms of 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid, which can be easily, economically and reproducibly prepared for use in a pharmaceutical formulation having consistent performance characteristics, which are excellent in for example stability and non-hygroscopicity. Also it is an object of this invention to provide processes for the preparation of, compositions containing and uses of, such polymorph forms.

Solution to Problem

Thus, the invention provides:

[1]
4-{[4-({[4-(2,2,2-Trifluoroethoxy)-1,2-benzisoxazol-3-yl]oxy}methyl)piperidin-1-yl]methyl}-tetrahydro-2H-pyran-4-carboxylic acid Polymorph Form III, which is characterized by a powder X-ray diffraction pattern (PXRD) obtained by irradiation with Cu-Kalpha radiation which includes main peaks at 2-theta 5.5, 10.1, 10.9, 13.9, 15.7, 18.5, 18.9, 20.8, 21.8 and 23.6(°), wherein each peak has a margin of error of +/−0.2(°);

[2]
4-{[4-({[4-(2,2,2-Trifluoroethoxy)-1,2-benzisoxazol-3-yl]oxy}methyl)piperidin-1-yl]methyl}-tetrahydro-2H-pyran-4-carboxylic acid Polymorph Form III, which is characterized by an infrared (IR) spectrum (diffuse reflection) which shows absorption bands at 4376-4370, 3525-3519, 3462, 2946-2940, 2127, 1713, 1624, 1537, 1508, 1441, 1368, 1287, 1157, 1121, 1103, 1063, 1034, 1013, 916, 870, 816, 781, 746, 733, 654, 619, 590 and 556 cm$^{-1}$, wherein each peak has a margin of error of +/−2 cm$^{-1}$.

[3]
4-{[4-({[4-(2,2,2-Trifluoroethoxy)-1,2-benzisoxazol-3-yl]oxy}methyl)piperidin-1-yl]methyl}-tetrahydro-2H-pyran-4-carboxylic acid Polymorph Form III as described in [1] or [2], which is further characterized by differential scanning calorimetry (DSC) in which it exhibits an endothermic event at 170° C., wherein the temperature has a margin of error of +/−1° C.;

[4]
4-{[4-({[4-(2,2,2-Trifluoroethoxy)-1,2-benzisoxazol-3-yl]oxy}methyl)piperidin-1-yl]methyl}-tetrahydro-2H-pyran-4-carboxylic acid Polymorph Form IV, which is characterized by a powder X-ray diffraction pattern (PXRD) obtained by irradiation with Cu-Kalpha radiation which includes main peaks at 2-theta 5.6, 9.8, 10.2, 11.3, 13.6, 13.8, 15.7, 17.0, 18.7, 19.3, 21.3 and 22.8(°), wherein each peak has a margin of error of +/−0.2(°);

[5]
4-{[4-({[4-(2,2,2-Trifluoroethoxy)-1,2-benzisoxazol-3-yl]oxy}methyl)piperidin-1-yl]methyl}-tetrahydro-2H-pyran-4-carboxylic acid Polymorph Form V, which is characterized by a powder X-ray diffraction pattern (PXRD) obtained by irradiation with Cu-Kalpha radiation which includes main peaks at 2-theta 5.2, 10.0, 10.3, 11.6, 15.5, 17.7, 18.6, 19.2, 20.5, 21.7, 22.4 and 24.3(°), wherein each peak has a margin of error of +/−0.2(°);

[6]
4-{[4-({[4-(2,2,2-Trifluoroethoxy)-1,2-benzisoxazol-3-yl]oxy}methyl)piperidin-1-yl]methyl}-tetrahydro-2H-pyran-4-carboxylic acid Polymorph Form V, which is characterized by an infrared (IR) spectrum (diffuse reflection) which shows absorption bands at 4381-4375, 4130, 2853, 2760, 1701, 1630, 1618, 1541, 1387, 1281, 1186, 1171, 1157, 1123, 1103, 1069, 1032, 1013, 991, 962, 917, 787, 748, 731, 660, and 650 cm$^{-1}$, wherein each peak has a margin of error of +/−2 cm$^{-1}$.

[7]
4-{[4-({[4-(2,2,2-Trifluoroethoxy)-1,2-benzisoxazol-3-yl]oxy}methyl)piperidin-1-yl]methyl}-tetrahydro-2H-pyran-4-carboxylic acid Polymorph Form V as described in [5] or [6], which is further characterized by differential scanning calorimetry (DSC) in which it exhibits an endothermic event at 169° C., wherein the temperature has a margin of error of +/−1° C.;

[8]
4-{[4-({[4-(2,2,2-Trifluoroethoxy)-1,2-benzisoxazol-3-yl]oxy}methyl)piperidin-1-yl]methyl}-tetrahydro-2H-pyran-4-carboxylic acid Polymorph Form VI, which is characterized by a powder X-ray diffraction pattern (PXRD) obtained by irradiation with Cu-Kalpha radiation which includes main peaks at 2-theta 10.3, 10.6, 11.4, 12.6, 18.8, 19.2, 19.5, 20.2, 21.2 and 21.7(°), wherein each peak has a margin of error of +/−0.2(°);

[9]
4-{[4-({[4-(2,2,2-Trifluoroethoxy)-1,2-benzisoxazol-3-yl]oxy}methyl)piperidin-1-yl]methyl}-tetrahydro-2H-pyran-4-carboxylic acid Polymorph Form VI, which is characterized by an infrared (IR) spectrum (diffuse reflection) which shows absorption bands at 4378-4372, 3944, 3467-3461, 3306, 2959, 2884, 2835, 1711, 1537, 970, 920, 883, and 785 cm$^{-1}$, wherein each peak has a margin of error of +/−2 cm$^{-1}$.

[10]
4-{[4-({[4-(2,2,2-Trifluoroethoxy)-1,2-benzisoxazol-3-yl]oxy}methyl)piperid in-1-yl]methyl}-tetrahydro-2H-pyran-4-carboxylic acid Polymorph Form VI as described in [8] or [9], which is further characterized by differential scanning calorimetry (DSC) in which it exhibits an endothermic event at 170° C., wherein the temperature has a margin of error of +/−1° C.;

[11]

A pharmaceutical composition including 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form as described in any one of [1] to [10], together with one or more pharmaceutically acceptable excipients;

[12]

4-{[4-({[4-(2,2,2-Trifluoroethoxy)-1,2-benzisoxazol-3-yl]oxy}methyl)piperidin-1-yl]methyl}-tetrahydro-2H-pyran-4-carboxylic acid Polymorph Form as described in any one of [1] to [10] for use as a medicament;

[13]

A use of 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form as described in any one of [1] to [10], or a pharmaceutical composition as described in [11], in the preparation of a medicament for the curative, palliative or prophylactic treatment of disease conditions mediated by 5-HT4 receptor activity;

[14]

A method of treating disease conditions mediated by 5-HT4 receptor activity, which comprises administering an effective amount of 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form as described in any one of [1] to [10], or a pharmaceutical composition as described in [11], to an animal, including a human, in need of such treatment;

[15]

A process for preparing 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form III as described in any one of [1] to [3], comprising the step of exposing Polymorph Form I under the relative humidity condition in the range of 60 to 100% at room temperature 15 to 35° C. or higher;

[16]

A process for preparing 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form III as described in any one of [1] to [3], comprising the step of exposing Polymorph Form I under the condition of 3 to 5% (v/v) water in alcohol, preferably ethyl alcohol or isopropyl alcohol;

[17]

A process for preparing 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form IV as described in [4], comprising the step of placing Polymorph Form III in atmosphere of 90 to 115° C., preferably 90° C. to 100° C.;

[18]

A process for preparing 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form V as described in any one of [5] to [7], comprising the step of exposing Polymorph Form I under a condition of forming Polymorph Form V without forming any other Polymorph Forms in the mixture of water and an organic solvent. More concretely, the process can be carried out by the method described, for example, in the below mentioned Example 7; and

[19]

A process for preparing 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form VI as described in any one of [8] to [10], comprising the step of exposing Polymorph Form I under the condition of forming Polymorph Form VI without forming any other Polymorph Forms in the mixture of water and an organic solvent.

Advantageous Effects of Invention

As mentioned above, it is an object of the present invention to find or prepare a crystalline or crystalline form in drug development from the various viewpoints including formulation and manufacturing of the drug. It has now been surprisingly found that this object has been achieved by the present invention, which provides crystalline forms of 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid known as Polymorph Form I, Polymorph Form II, Polymorph Form III, Polymorph Form IV, Polymorph Form V and Polymorph Form VI.

No pharmaceutically suitable crystalline forms of the said compound have been identified in spite of great efforts of those skilled in the art.

All of the polymorph forms of the present invention have an excellent and unexpected advantage over the white solid disclosed in the prior art WO2006/090224. Polymorph Form I and Polymorph Form II are found to be more stable than the white solid disclosed in the prior art WO2006/090224. In addition, in terms of hygroscopicity both of them have an excellent and unexpected advantage over the white solid disclosed in the prior art WO2006/090224.

In addition, Polymorph Form III and Polymorph Form V have also lower hygroscopicity in comparison with the white solid disclosed in the prior art WO2006/090224.

As mentioned above, Polymorph Form I has a good solid-state stability comparing with white solid disclosed in the prior art WO2006/090224 but Polymorph Form III has more excellent solid-state stability than Polymorph Form I.

Polymorph Form IV is a good intermediate of Polymorph Form III because Polymorph Form IV is easy to convert to Polymorph Form III when it is just cooled. Polymorph Form VI is also a good intermediate of Polymorph Form III because Polymorph Form VI is easy to convert to Polymorph Form III when it is just dried.

Furthermore the Polymorph Forms of the present invention are found to be applicable for a large scale synthesis. They have acceptable solid-state properties for solid-dosage form development.

BRIEF DESCRIPTION OF DRAWINGS

FIG. 1 shows the PXRD pattern of a reference product obtained from the method of preparing 4-{[4-({[4-(2,2,2-trifluoroethoxy)-1,2-benzisoxazol-3-yl]oxy}methyl)piperidin-1-yl]-methyl}-tetrahydro-2H-pyran-4-carboxylic acid described in Example 1 of WO2006/090224.

FIG. 2 shows the PXRD pattern of 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form I.

FIG. 3 shows the IR spectra (KBr) of 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form I.

FIG. 4 shows the IR spectra (diffuse reflection) of 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form I.

FIG. 5 shows the PXRD pattern of 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form II.

FIG. 6 shows the IR spectra (KBr) of 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form II.

FIG. 7 shows the PXRD pattern of 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form III.

FIG. 8 shows the IR spectra (diffuse reflection) of 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form III FIG. 9 shows the PXRD pattern of 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form IV.

FIG. 10 shows the PXRD pattern of 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form V.

FIG. 11 shows the IR spectra (diffuse reflection) of 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form V.

FIG. 12 shows the PXRD pattern of 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form VI.

FIG. 13 shows the IR spectra (diffuse reflection) of 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form VI.

FIG. 14 shows change in mass % (weight gain %) of Polymorph Form I, Polymorph Form III, Polymorph Form V and the white solid disclosed in the prior art WO2006/090224 under each RH condition.

DESCRIPTION OF EMBODIMENTS

Accordingly, the present invention provides crystalline 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form I, which is characterized by a powder X-ray diffraction pattern (PXRD) obtained by irradiation with Cu-Kalpha radiation which includes main peaks at 2-theta 5.9, 9.3, 9.8, 11.9, 13.7, 14.3, 15.0, 17.8, 18.2-19.3, 19.7, 22.6, 23.4-24.5 and 24.9(°), wherein each peak has a margin of error of +/−0.2(°);

4-{[4-({[4-(2,2,2-Trifluoroethoxy)-1,2-benzisoxazol-3-yl]oxy}methyl)piperidin-1-yl]methyl}-tetrahydro-2H-pyran-4-carboxylic acid Polymorph Form I as described above, which is further characterized by differential scanning calorimetry (DSC) in which it exhibits an endothermic thermal event at 169° C., wherein the temperature has a margin of error of +/−1° C.;

4-{[4-({[4-(2,2,2-Trifluoroethoxy)-1,2-benzisoxazol-3-yl]oxy}methyl)piperidin-1-yl]methyl}-tetrahydro-2H-pyran-4-carboxylic acid Polymorph Form I as described above, which is yet further characterized by an infrared (IR) spectrum (KBr) which shows absorption bands at 2948, 1723, 1615, 1535, 1506, 1437, 1383, 1366, 1287, 1262, 1245, 1180, 1164, 1120, 1095, 1059, 1032, 992, 974, 935, 918, 869, 858, 828, 784, 746, 732, 654 and 556 (cm$^{-1}$), wherein each peak has a margin of error of +/−2 (cm$^{-1}$);

4-{[4-({[4-(2,2,2-Trifluoroethoxy)-1,2-benzisoxazol-3-yl]oxy}methyl)piperidin-1-yl]methyl}-tetrahydro-2H-pyran-4-carboxylic acid Polymorph Form II, which is characterized by a powder X-ray diffraction pattern (PXRD) obtained by irradiation with Cu-Kalpha radiation which includes main peaks at 2-theta 5.8, 9.7, 10.5, 11.8, 12.4, 13.5, 14.2, 14.6-14.9, 15.4, 17.8, 18.2, 19.9-20.5, 21.2, 21.8, 23.6, 24.1 and 24.6(°), wherein each peak has a margin of error of +/−0.2(°);

4-{[4-({[4-(2,2,2-Trifluoroethoxy)-1,2-benzisoxazol-3-yl]oxy}methyl)piperidin-1-yl]methyl}-tetrahydro-2H-pyran-4-carboxylic acid Polymorph Form II as described above, which is further characterized by differential scanning calorimetry (DSC) in which it exhibits an endothermic event at about 167-169° C.; and 4-{[4-({[4-(2,2,2-Trifluoroethoxy)-1,2-benzisoxazol-3-yl]oxy}methyl)piperidin-1-yl]methyl}-tetrahydro-2H-pyran-4-carboxylic acid Polymorph Form II, as described above, which is further characterized by an infrared (IR) spectrum (KBr) which shows absorption bands at 2950, 1724, 1614, 1534, 1507, 1438, 1383, 1366, 1287, 1262, 1245, 1180, 1164, 1121, 1095, 1059, 1031, 992, 974, 935, 918, 869, 857, 828, 784, 746, 732, 654 and 555 (cm$^{-1}$), wherein each peak has a margin of error of +/−2 (cm$^{-1}$).

4-{[4-({[4-(2,2,2-Trifluoroethoxy)-1,2-benzisoxazol-3-yl]oxy}methyl)piperidin-1-yl]methyl}-tetrahydro-2H-pyran-4-carboxylic acid Polymorph Form III, which is characterized by a powder X-ray diffraction pattern (PXRD) obtained by irradiation with Cu-Kalpha radiation which includes main peaks at 2-theta 5.5, 10.1, 10.9, 13.9, 15.7, 18.5, 18.9, 20.8, 21.8 and 23.6(°), wherein each peak has a margin of error of +/−0.2(°);

4-{[4-({[4-(2,2,2-Trifluoroethoxy)-1,2-benzisoxazol-3-yl]oxy}methyl)piperidin-1-yl]methyl}-tetrahydro-2H-pyran-4-carboxylic acid Polymorph Form III as described above, which is further characterized by differential scanning calorimetry (DSC) in which it exhibits an endothermic event at 170° C., wherein the temperature has a margin of error of +/−1° C.;

4-{[4-({[4-(2,2,2-Trifluoroethoxy)-1,2-benzisoxazol-3-yl]oxy}methyl)piperidin-1-yl]methyl}-tetrahydro-2H-pyran-4-carboxylic acid Polymorph Form IV, which is characterized by a PXRD obtained by irradiation with Cu-Kalpha radiation which includes main peaks at 2-theta 5.6, 9.8, 10.2, 11.3, 13.6, 13.8, 15.7, 17.0, 18.7, 19.3, 21.3 and 22.8(°), wherein each peak has a margin of error of +/−0.2(°);

4-{[4-({[4-(2,2,2-Trifluoroethoxy)-1,2-benzisoxazol-3-yl]oxy}methyl)piperidin-1-yl]methyl}-tetrahydro-2H-pyran-4-carboxylic acid Polymorph Form V, which is characterized by a powder X-ray diffraction pattern (PXRD) obtained by irradiation with Cu-Kalpha radiation which includes main peaks at 2-theta 5.2, 10.0, 10.3, 11.6, 15.5, 17.7, 18.6, 19.2, 20.5, 21.7, 22.4 and 24.3(°), wherein each peak has a margin of error of +/−0.2(°);

4-{[4-({[4-(2,2,2-Trifluoroethoxy)-1,2-benzisoxazol-3-yl]oxy}methyl)piperidin-1-yl]methyl}-tetrahydro-2H-pyran-4-carboxylic acid Polymorph Form V as described above, which is further characterized by differential scanning calorimetry (DSC) in which it exhibits an endothermic event at 169° C., wherein the temperature has a margin of error of +/−1° C.;

4-{[4-({[4-(2,2,2-Trifluoroethoxy)-1,2-benzisoxazol-3-yl]oxy}methyl)piperidin-1-yl]methyl}-tetrahydro-2H-pyran-4-carboxylic acid Polymorph Form VI, which is characterized by a powder X-ray diffraction pattern (PXRD) obtained by irradiation with Cu-Kalpha radiation which includes main peaks at 2-theta 10.3, 10.6, 11.4, 12.6, 18.8, 19.2, 19.5, 20.2, 21.2 and 21.7 (°), wherein each peak has a margin of error of +/−0.2 (°);

4-{[4-({[4-(2,2,2-Trifluoroethoxy)-1,2-benzisoxazol-3-yl]oxy}methyl)piperidin-1-yl]methyl}-tetrahydro-2H-pyran-4-carboxylic acid Polymorph Form VI as described above, which is further characterized by differential scanning calorimetry (DSC) in which it exhibits an endothermic event at 170° C., wherein the temperature has a margin of error of +/−1° C.

As a further aspect of the invention, there is provided 4-{[4-({[4-(2,2,2-Trifluoroethoxy)-1,2-benzisoxazol-3-yl]oxy}methyl)piperidin-1-yl]methyl}-tetrahydro-2H-pyran-4-carboxylic acid Polymorph Form of the present invention for use as a medicament.

As a yet further aspect of the invention, there is provided the use of 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form of the present invention in the manufacture of a medicament for the treatment of any disease which mediated by a 5-HT4 receptor antagonist, particularly for the curative, prophylactic or palliative treatment of gastroesophageal reflux disease (GERD), gastrointestinal disease, gastric motility disorder, non-ulcer dyspepsia, functional dyspepsia (FD), irritable bowel syndrome (IBS), constipation, dyspepsia, esophagitis, gastroesophageal disease, gastritis, nausea, central nervous system disease, Alzheimer's disease, cognitive disorder, emesis, migraine, neurological disease, pain, cardiovascular disorders, cardiac failure, heart arrhythmia, diabetes, and apnea syndrome.

As an alternative aspect, there is provided a method for the treatment of any disease which mediated by a 5-HT4 receptor antagonist, particularly for the curative, prophylactic or palliative treatment of gastroesophageal reflux disease (GERD), gastrointestinal disease, gastric motility disorder, non-ulcer dyspepsia, functional dyspepsia (FD), irritable bowel syndrome (IBS), constipation, dyspepsia, esophagitis, gastroesophageal disease, gastritis, nausea, central nervous system disease, Alzheimer's disease, cognitive disorder, emesis, migraine, neurological disease, pain, cardiovascular disorders, cardiac failure, heart arrhythmia, diabetes, and apnea syndrome, including administration of a therapeutically effective amount of 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form of the present invention to an animal, including a human, in need of such treatment.

The 4-{[4-({[4-(2,2,2-trifluoroethoxy)-1,2-benzisoxazol-3-yl]oxy}methyl)piperidin-1-yl]-methyl}-tetrahydro-2H-pyran-4-carboxylic acid Polymorph Form of the present invention is useful for the general treatment of disease conditions mediated by 5-HT4 receptor activity.

The 4-{[4-({[4-(2,2,2-trifluoroethoxy)-1,2-benzisoxazol-3-yl]oxy}methyl)piperidin-1-yl]-methyl}-tetrahydro-2H-pyran-4-carboxylic acid Polymorph Form of the present invention can also be useful for the treatment of a disorder or condition selected from the group consisting of gastroesophageal reflux disease (GERD), gastrointestinal, disease, gastric motility disorder, non-ulcer dyspepsia, functional dyspepsia (FD), irritable bowel syndrome (IBS), constipation, dyspepsia, esophagitis, gastroesophageal disease, gastritis, nausea, central nervous system disease, Alzheimer's disease, cognitive disorder, emesis, migraine, neurological disease, pain, cardiovascular disorders, cardiac failure, heart arrhythmia, diabetes, and apnea syndrome.

Synthetic routes for the preparation of 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid are described in WO2006/090224 and in Example Section below.

4-{[4-({[4-(2,2,2-Trifluoroethoxy)-1,2-benzisoxazol-3-yl]oxy}methyl)piperidin-1-yl]methyl}-tetrahydro-2H-pyran-4-carboxylic acid Polymorph Form I can be prepared by crystallization from a solution of 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid in ethyl acetate.

Organic solvents including ethyl acetate can be used for the crystallization of Polymorph Form I. Preferably examples of solvents which can be mixed with ethyl acetate include one or more than one solvents selected from: water; alcohols such as methanol, ethanol, and propanol; ethers such as diethyl ether, tert-butylmethyl ether, dioxane, and tetrahydrofuran; hydrocarbons such as hexane, heptane, cyclohexane, dichloromethane, chloroform, benzene, toluene, and xylene; ketones such as acetone and methylethylketone; amides such as dimethylformamide and dimethylacetamide; and sulfoxides such as dimethylsulfoxide.

Depending on the concentration of the compound, the reducing rate of temperature at the recrystallization is generally lower than 100° C./hour at the concentration of about 0.1 mg/mL to about 200 mg/mL. Preferably lower than 50° C./hour, more preferably lower than 20° C./hour, and most preferably lower than 5° C./hour can be applied for the recrystallization.

4-{[4-({[4-(2,2,2-Trifluoroethoxy)-1,2-benzisoxazol-3-yl]oxy}methyl)piperidin-1-yl]methyl}-tetrahydro-2H-pyran-4-carboxylic acid Polymorph Form II can be prepared by placing Polymorph Form I at a temperature of 110° C. or higher temperature.

4-{[4-({[4-(2,2,2-Trifluoroethoxy)-1,2-benzisoxazol-3-yl]oxy}methyl)piperidin-1-yl]methyl}-tetrahydro-2H-pyran-4-carboxylic acid Polymorph Form III may be prepared by transforming from Polymorph Form I under a high relative humidity condition. The relative humidity can be varied in the range of 60 to 100% at room temperature in the range of 15 to 35° C. or higher.

In addition Polymorph Form III may be prepared by transforming from Polymorph Form I in a mixture of water and isopropyl alcohol optionally using the seed of Polymorph Form III. The condition of 3 to 5% (v/v) Water in alcohol can be used to obtain Polymorph Form III without forming any other Polymorph Forms. Examples of preferable alcohol include, not limited to, ethanol, isopropyl alcohol and the like.

4-{[4-({[4-(2,2,2-Trifluoroethoxy)-1,2-benzisoxazol-3-yl]oxy}methyl)piperidin-1-yl]methyl}-tetrahydro-2H-pyran-4-carboxylic acid Polymorph Form IV can be prepared by transforming from Polymorph Form III at 90 to 100° C. Polymorph Form IV is stable up to 115° C.

4-{[4-({[4-(2,2,2-Trifluoroethoxy)-1,2-benzisoxazol-3-yl]oxy}methyl)piperidin-1-yl]methyl}-tetrahydro-2H-pyran-4-carboxylic acid Polymorph Form V can be prepared by transforming from Polymorph Form I under the suspension condition in water.

In addition, Polymorph Form V can be prepared by transforming from Polymorph Form I in a mixture of water and an organic solvent. The ratio of water in an organic solvent depends on the solvent used. For example, in the case of tetrahydrofuran, 10% (v/v) or higher water in tetrahydrofuran can be used to obtain Polymorph Form V. In the case of isopropylalcohol, 20% (v/v) or higher water in isopropylalcohol can be used to obtain Polymorph Form V. In the case of acetone or acetonitrile, 50% (v/v) or higher water in acetone or acetonitrile can be used to obtain Polymorph Form V.

Examples of organic solvent include, but not limited to, tetrahydrofuran, isopropylalcohol, ethanol, acetone, acetonitrile, and the like.

4-{[4-({[4-(2,2,2-Trifluoroethoxy)-1,2-benzisoxazol-3-yl]oxy}methyl)piperidin-1-yl]methyl}-tetrahydro-2H-pyran-4-carboxylic acid Polymorph Form VI can be prepared by transforming from Polymorph Form I in a mixture of water and an organic solvent. The ratio of water in an organic solvent depends on the solvent used. For example, in the case of acetone, 5 to 10% (v/v) water in acetone can be used to obtain Polymorph Form VI. In the case of acetonitrile, 5 to 10% (v/v) water in acetonitrile can be used to obtain Polymorph Form VI. In the case of tetrahydrofuran, 5% (v/v) water in tetrahydrofuran can be used to obtain Polymorph Form VI.

Examples of organic solvent include, but not limited to, tetrahydrofuran, isopropylalcohol, ethanol, acetonitrile, acetone, and the like.

The 4-{[4-({[4-(2,2,2-trifluoroethoxy)-1,2-benzisoxazol-3-yl]oxy}methyl)piperidin-1-yl]-methyl} tetrahydro-2H-pyran-4-carboxylic acid Polymorph Form of the present invention can be administered alone or in combination with one or more other drugs (or as any combination thereof). Generally, they will be administered as a formulation in association with one or more pharmaceutically acceptable excipients. The term 'excipient' is used herein to describe any ingredient other than the compound of the invention. The choice of excipient will to a large extent depend on factors such as the particular mode of administration, the effect of the excipient on solubility and stability, and the nature of the dosage form.

Thus, as a further aspect of the present invention, there is provided a pharmaceutical composition including 4-{[4-({[4-(2,2,2-trifluoroethoxy)-1,2-benzisoxazol-3-yl]oxy}methyl)-piperidin-1-yl]methyl} tetrahydro-2H-pyran-4-carboxylic acid Polymorph Form and one or more suitable excipients. The composition is suitable for the treatment of disease conditions mediated by 5-HT4 receptor activity.

The term "Polymorph Form(s)" as used herein, includes Polymorph Form I, Polymorph Form II, Polymorph Form III, Polymorph Form IV, Polymorph Form V, and/or Polymorph Form VI.

Weight purity of 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form of the present invention is not limited, but preferably an essentially pure Polymorph Form can be used for specific embodiments in this invention.

For the avoidance of doubt, the expression 'essentially pure' when used herein means at least 90% by weight purity. More preferably, 'essentially pure' means at least 95% by weight purity and most preferably means at least 98% by weight purity.

References herein to "treatment" include references to curative, palliative and prophylactic treatment.

For non-human animal administration, the term 'pharmaceutical' as used herein may be replaced by 'veterinary.'

Pharmaceutical compositions suitable for the delivery of Polymorph Form of the invention and methods for the preparation will be readily apparent to those skilled in the art. Such compositions and methods for the preparation may be found, for example, in Remington's Pharmaceutical Sciences, 19th Edition (Mack Publishing Company, 1995).

Oral Administration

The Polymorph Form of the invention may be administered orally. Oral administration may involve swallowing, so that the compound enters the gastrointestinal tract, and/or buccal, lingual, or sublingual administration by which the compound enters the blood stream directly from the mouth.

Formulations suitable for oral administration include solid, semi-solid and liquid systems such as tablets; soft or hard capsules containing multi- or nano-particulates, liquids, or powders; lozenges (including liquid-filled); chews; gels; fast dispersing dosage forms; films; ovules; sprays; and buccal or mucoadhesive patches.

Liquid formulations include suspensions, solutions, syrups and elixirs. Such formulations may be employed as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid taken from a sachet etc.

The Polymorph Form of the invention may also be used in fast-dissolving, fast-disintegrating dosage forms such as those described in Expert Opinion in Therapeutic Patents 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate. Tablets may also optionally comprise surface active agents, such as sodium lauryl sulfate and polysorbate 80, and glidants such as silicon dioxide and talc. When present, surface active agents may be contained from 0.2 weight % to 5 weight % of the tablet, and glidants may be contained from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in Pharmaceutical Dosage Forms: Tablets, Vol. 1, by H. Lieberman and L. Lachman (Marcel Dekker, New York, 1980).

Consumable oral films for human or veterinary use are typically pliable water-soluble or water-swellable thin film dosage forms which may be rapidly dissolving or mucoadhesive and typically comprise a Polymorph Form in accordance with the invention, a film-forming polymer, a binder, a solvent, a humectant, a plasticizer, a stabilizer or emulsifier, a viscosity-modifying agent and a solvent. Some components of the formulation may perform more than one function.

The Polymorph Form of the invention may be water-soluble or insoluble depending upon circumstances or conditions. A water-soluble compound typically may be contained from 1 weight % to 80 weight %, more typically from 20 weight % to 50 weight %, of the solutes. Less soluble compounds may be contained in a greater proportion of the composition, typically up to 88 weight % of the solutes. Alternatively, the Polymorph Form of the invention may be in the form of multiparticulate beads.

The film-forming polymer may be selected from natural polysaccharides, proteins, or synthetic hydrocolloids and is typically present in the range of 0.01 to 99 weight %, more typically in the range of 30 to 80 weight %.

Other possible ingredients include anti-oxidants, colorants, flavourings and flavour enhancers, preservatives, salivary stimulating agents, cooling agents, co-solvents (including oils), emollients, bulking agents, anti-foaming agents, surfactants and taste-masking agents.

Films in accordance with the invention are typically prepared by evaporative drying of thin aqueous films coated onto a peelable backing support or paper.

This may be done in a drying oven or tunnel, typically a combined coater dryer, or by freeze-drying or vacuuming.

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in Pharmaceutical Technology On-line, 25(2), 1-14, by Verma et al. (2001). The use of chewing gum to achieve controlled release is described in WO 00/35298.

Parenteral Administration

The Polymorph Form of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular, intrasynovial and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilization, may readily be accomplished using standard pharmaceutical techniques well known to those skilled in the art.

Formulations for parenteral administration may be formulated to be immediate and/or modified release. Modified release formulations include delayed-, sustained-, pulsed-, controlled-, targeted and programmed release. Thus the Polymorph Form of the invention may be formulated as a suspension or as a solid, semi-solid, or thixotropic liquid for administration as an implanted depot providing modified release of the active compound. Examples of such formulations include drug-coated stents and semi-solids and suspensions comprising drug-loaded poly(lactic-co-glycolic acid) (PLGA) microspheres.

Topical Administration

The Polymorph Form of the invention may also be administered topically, (intra)dermally, or transdermally to the skin or mucosa. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958, by Finnin and Morgan (October 1999).

Other means of topical administration include delivery by electroporation, iontophoresis, phonophoresis, sonophoresis and microneedle or needle-free (e.g. Powderject (trade mark), Bioject (trade mark), etc.) injection. Topical administration may also be achieved using a patch, such as a transdermal iontophoretic patch.

Formulations for topical administration may be formulated to be immediate and/or modified release. Modified release formulations include delayed-, sustained-, pulsed-, controlled-, targeted and programmed release.

The Polymorph Form of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler, as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane, or as nasal drops. For intranasal use, the powder may comprise a bioadhesive agent, for example, chitosan or cyclodextrin.

The pressurized container, pump, spray, atomizer, or nebulizer contains a solution or suspension of a Polymorph Form in accordance with the invention comprising, for example, ethanol, aqueous ethanol, or a suitable alternative agent for dispersing, solubilizing, or extending release of the active, a propellant(s) as solvent and an optional surfactant, such as sorbitan trioleate, oleic acid, or an oligolactic acid.

Prior to use in a dry powder or suspension formulation, the drug product is micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomizer using electrohydrodynamics to produce a fine mist may contain from 1 micro g to 20 mg of the compound of the invention per actuation and the actuation volume may vary from 1 micro L to 100 micro L. A typical formulation may comprise a Polymorph Form in accordance with the invention, propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, PLGA. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from 1 micro g to 20 mg of the compound. The overall daily dose will typically be in the range of 1 micro g to 100 mg which may be administered in a single dose or, more usually, as divided doses throughout the day.

Rectal/Intravaginal Administration

The Polymorph Form of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

Ocular/Aural Administration

The Polymorph Form of the invention may also be administered directly to the eye or ear, typically in the form of drops of a micronized suspension or solution in isotonic, pH-adjusted, sterile saline. Other formulations suitable for ocular and aural administration include ointments, gels, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gellan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

Other Technologies

The Polymorph Form of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubilizer. Most commonly used for these purposes are alpha-, beta- and gamma-cyclodextrins, examples of which may be found in International Patent Publication Nos. WO 91/11172, WO 94/02518, WO 98/55148 and Evrard, B., et al., Journal of Controlled Release 96 (3), pp. 403-410, 2004.

Dosage

For treating or preventing the disease conditions mediated by 5-HT4 receptor activity such as gastrointestinal diseases, a suitable dosage level of the Polymorph Form of this invention is about 0.0001 to 1000 mg per day, preferably about 0.001 to 100 mg per day, and more preferably about 0.005 to 50 mg per day, and most preferably 1 to 50 mg per day of the active compound. The compounds may be administered on a regimen of 1 to 4 times per day. In some cases, however, a dosage outside these limits may be used.

These dosages are based on an average human subject having a weight of about 60 kg to 70 kg. The physician will readily be able to determine doses for subjects whose weight falls outside this range, such as infants and the elderly. For the avoidance of doubt, references herein to "treatment" include references to curative, palliative and prophylactic treatment.

The Polymorph Form of the present invention may also optionally be combined with another pharmacologically active compound, or with two or more other pharmacologically active compounds, particularly for the treatment of disease conditions mediated by 5-HT4 receptor activity. For example, the Polymorph Form of the present invention, as defined above, may be administered simultaneously, sequentially or separately in combination with one or more agents selected from:

an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;

a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;

a barbiturate sedative, e.g. amobarbital, aprobarbital, butabarbital, butabital, mephobarbital, metharbital, methohexital, pentobarbital, phenobartital, secobarbital, talbutal, thiamylal or thiopental;

a benzodiazepine having a sedative action, e.g. chlordiazepoxide, clorazepate, diazepam, flurazepam, lorazepam, oxazepam, temazepam or triazolam;

an H1 antagonist having a sedative action, e.g. diphenhydramine, pyrilamine, promethazine, chlorpheniramine or chlorcyclizine;

a sedative such as glutethimide, meprobamate, methaqualone or dichloralphenazone;

a skeletal muscle relaxant, e.g. baclofen, carisoprodol, chlorzoxazone, cyclobenzaprine, methocarbamol or orphrenadine;

an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex(registered trademark), a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-dihydro-2(1H)-quinolinone;

an alpha-adrenergic, e.g. doxazosin, tamsulosin, clonidine, guanfacine, dexmedetomidine, modafinil, or 4-amino-6,7-dimethoxy-2-(5-methane-sulfonamido-1,2,3,4-tetrahydroisoquinol-2-yl)-5-(2-pyridyl) quinazoline;

a tricyclic antidepressant, e.g. desipramine, imipramine, amitriptyline or nortriptyline;

an anticonvulsant, e.g. carbamazepine, lamotrigine, topiramate or valproate;

a tachykinin (NK) antagonist, particularly an NK-3, NK-2 or NK-1 antagonist, e.g., (alphaR,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis(trifluoromethyl)phenyl] ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);

a muscarinic antagonist, e.g. oxybutynin, tolterodine, propiverine, trospium chloride, darifenacin, solifenacin, temiverine and ipratropium;

a COX-2 selective inhibitor, e.g. celecoxib, rofecoxib, parecoxib, valdecoxib, deracoxib, etoricoxib, or lumiracoxib;

a coal-tar analgesic, in particular paracetamol;

a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion(registered trademark) or sarizotan;

a vanilloid receptor agonist (e.g. resiniferatoxin) or antagonist (e.g. capsazepine);

a transient receptor potential cation channel subtype (V1, V2, V3, V4, M8, A1) agonist or antagonist;

a beta-adrenergic such as propranolol;

a local anaesthetic such as mexiletine;

a corticosteroid such as dexamethasone;

a 5-HT receptor agonist or antagonist, particularly a 5-HT1B/1D agonist such as eletriptan, sumatriptan, naratriptan, zolmitriptan or rizatriptan;

a 5-HT2A receptor antagonist such as R(+)-alpha-(2,3-dimethoxy-phenyl)-1-[2-(4-fluorophenylethyl)]-4-piperidinemethanol (MDL-100907);

a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;

Tramadol(registered trademark);

a PDEV inhibitor, such as

5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)-pyrazino[2',1':6,1]-pyrido[3,4-b] indole-1,4-dione (IC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-azetidinyl)-2,6-dihydro-7H-pyrazolo[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl)pyrrolidin-1-yl]-N-(pyrimidin-2-ylmethyl) pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;

an alpha-2-delta ligand such as gabapentin, pregabalin, 3-methylgabapentin, (1alpha,3 alpha,5alpha)(3-aminomethyl-bicyclo[3.2.0]hept-3-yl)-acetic acid, (3S,5R)-3 aminomethyl-5 methyl-heptanoic acid, (3S,5R)-3 amino-5 methyl-heptanoic acid, (3S,5R)-3 amino-5 methyl-octanoic acid, (2S,4S)-4-(3-chlorophenoxy) proline, (2S,4S)-4-(3-fluorobenzyl)-proline, [(1R,5R,6S)-6-(aminomethyl)bicyclo[3.2.0]hept-6-yl]acetic acid, 3-(1-aminomethyl-cyclohexylmethyl)-4H-[1,2,4] oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (3S,5R)-3 aminomethyl-5 methyl-octanoic acid, (3S,5R)-3 amino-5 methyl-nonanoic acid, (3S,5R)-3 amino-5 methyl-octanoic acid, (3R,4R,5R)-3-amino-4,5-dimethyl-heptanoic acid and (3R,4R,5R)-3-amino-4,5-dimethyl-octanoic acid;

a cannabinoid;

a metabotropic glutamate subtype 1 receptor (mGluR1) antagonist;

a serotonin reuptake inhibitor such as sertraline, sertraline metabolite desmethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;

a noradrenaline (norepinephrine) reuptake inhibitor, such as maprotiline, lofepramine, mirtazapine, oxaprotiline, fezolamine, tomoxetine, mianserin, buproprion, buproprion metabolite hydroxybuproprion, nomifensine and viloxazine (Vivalan (registered trademark)), especially a selective noradrenaline reuptake inhibitor such as reboxetine, in particular (S,S)-reboxetine;

a dual serotonin-noradrenaline reuptake inhibitor, such as venlafaxine, venlafaxine metabolite O-desmethylvenlafaxine, clomipramine, clomipramine metabolite desmethylclomipramine, duloxetine, milnacipran and imipramine;

an inducible nitric oxide synthase (iNOS) inhibitor such as

S-[2-[(1-iminoethyl)amino]ethyl]-L-homocysteine,
S-[2-[(1-iminoethyl)-amino]ethyl]-4,4-dioxo-L-cysteine,
S-[2-[(1-iminoethyl)amino]ethyl]-2-methyl-L-cysteine,
(2S,5Z)-2-amino-2-methyl-7-[(1-iminoethyl)amino]-5-heptenoic acid,
2-[[(1R,3S)-3-amino-4-hydroxy-1-(5-thiazolyl)-butyl]thio]-5-chloro-3-pyridinecarbonitrile;
2-[[(1R,3S)-3-amino-4-hydroxy-1-(5-thiazolyl)butyl]thio]-4-chlorobenzonitrile,
(2S,4R)-2-amino-4-[[2-chloro-5-(trifluoromethyl)phenyl]thio]-5-thiazolebutanol,
2-[[(1R,3S)-3-amino-4-hydroxy-1-(5-thiazolyl)butyl]thio]-6-(trifluoromethyl)-3 pyridinecarbonitrile,
2-[[(1R,3S)-3-amino-4-hydroxy-1-(5-thiazolyl)butyl]thio]-5-chlorobenzonitrile,
N-[4-[2-(3-chlorobenzylamino)ethyl]phenyl]thiophene-2-carboxamidine, or guanidinoethyldisulfide;

an acetylcholinesterase inhibitor such as donepezil;
a prostaglandin E2 subtype 4 (EP4) antagonist such as
N-[({2-[4-(2-ethyl-4,6-dimethyl-1H-imidazo[4,5-c]pyridin-1-yl)phenyl]ethyl}amino)-carbonyl]-4-methylbenzenesulfonamide or
4-[(1S)-1-({[5-chloro-2-(3-fluorophenoxy)pyridin-3-yl]carbonyl}amino)ethyl]benzoic acid;

a leukotriene B4 antagonist; such as
1-(3-biphenyl-4-ylmethyl-4-hydroxy-chroman-7-yl)-cyclopentanecarboxylic acid (CP-105696),
5-[2-(2-Carboxyethyl)-3-[6-(4-methoxyphenyl)-5E-hexenyl]oxyphenoxy]-valeric acid (ONO-4057) or DPC-11870, a 5-lipoxygenase inhibitor, such as zileuton,
6-[(3-fluoro-5-[4-methoxy-3,4,5,6-tetrahydro-2H-pyran-4-yl])phenoxy-methyl]-1-methyl-2-quinolone (ZD-2138), or
2,3,5-trimethyl-6-(3-pyridylmethyl), 1,4-benzoquinone (CV-6504);

a sodium channel blocker, such as lidocaine;
a calcium channel blocker, such as ziconotide, zonisamide, mibefradil;
a 5-HT3 antagonist, such as ondansetron;
a chemotherapy drug such as oxaliplatin, 5-fluorouracil, leukovolin, paclitaxel;
a calcitonin gene related peptide (CGRP) antagonist;
a bradykinin (BK1 and BK2) antagonist;
a voltage gated sodium dependent channel blocker ($Na_{v1.3}$, $Na_{v1.7}$, $Na_{v1.8}$);
a voltage dependent calcium channel blocker (N-type, T-type);
a P2X (ion channel type ATP receptor) antagonist;
an acid-sensing ion channel (ASIC1a, ASIC3) antagonist;
an Angiotensin AT2 antagonist;
a Chemokine CCR2B receptor antagonist;
a Cathepsin (B, S, K) inhibitor;
a sigma1 receptor agonist or antagonist;
and the pharmaceutically acceptable salts and solvates thereof.

Such combinations offer significant advantages, including synergistic activity, in therapy.

Combination Drug and Kit

One embodiment of the present invention is a combination of the Polymorph Form of the present invention, and a drug for gastrointestinal diseases, which is different from the polymorph form of the present invention. A "combination" according to the invention may be present as a "fix combination" or as a "kit of parts combination". A "fix combination" is defined as a combination wherein the (i) at least one drug for gastrointestinal diseases, which is different from the polymorph form of the present invention, and (ii) the Polymorph Form are present in one unit. A "kit of parts combination" is defined as a combination wherein the (i) at least one drug for gastrointestinal diseases, which is different from the polymorph form of the present invention, and (ii) the Polymorph Form are present in more than one unit. The components of the "kit of parts combination" may be administered simultaneously, sequentially or separately. The molar ratio of the drug for gastrointestinal diseases, which is different from the polymorph form of the present invention, to the Polymorph Form used according to the invention is within the range of from 1:100 to 100:1, such as from 1:50 to 50:1 or from 1:20 to 20:1 or from 1:10 to 10:1. The two drugs may be administered separately in the same ratio. Examples of acid secretion inhibiting agents are other 5-HT4 agonists, proton pump inhibitors, H2 receptor antagonists, and drugs for IBS or constipations. These examples are H2 blocking agents such as cimetidine, ranitidine; as well as proton pump inhibitors such as pyridinylmethylsulfinyl benzimidazoles such as omeprazole, esomeprazole, lansoprazole, pantoprazole, rabeprazole or related substances such as leminoprazole.

The present invention extends to a combination comprising 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form I and/or Polymorph Form II and one or more therapeutic agents, such as those listed above, for simultaneous, separate or sequential use in the curative, prophylactic or palliative treatment of disease conditions mediated by 5-HT4 receptor activity.

EXAMPLES

The following example is for reference only.

Analysis

Powder X-Ray Diffraction (PXRD)

The PXRD analyses are performed using a Rigaku RINT-TTR X-ray powder diffractometer using Cu-Kalpha radiation. The samples can also be measured under the high/low temperature condition by using the attachment of the variant-temperature sample holder. The instrument is equipped with a fine focus X-ray tube. The tube voltage and amperage are set to 50 kV and 300 mA respectively. The divergence and scattering slits are set at 0.5° and the receiving slit is set at 0.15 mm. Diffracted radiation is detected by a NaI scintillation detector. A theta-two theta continuous scan at 4°/min (step size 0.02°) from 3 to 40(°) 2-theta is used. A silicon standard is analyzed to check the machine alignment. Data are collected and analyzed using-Rigaku X-ray system. Samples are prepared for analysis by placing them in an aluminum sample holder that is horizontally rotated at 60 rpm during data acquisition.

Thermogravimetry/Differential Thermal Analysis (TG/DTA)

TG/DTA is performed using Seiko 6200R system. The sample is placed into an aluminum TG/DTA pan. Each sample is heated under a nitrogen purge at a rate of 5° C./min, up to a final temperature of 300° C. Indium metal is used as the calibration standard. Reported values are rounded and should therefore be considered approximate.
Differential Scanning Calorimetry (DSC)

DSC analysis is performed using Mettler Toledo DSC822. The sample is placed into an aluminum DSC pan and the weight accurately recorded. The pan is covered with a lid with a pinhole and then crimped. Each sample is heated under a nitrogen purge at a rate of 5° C./min, up to a final temperature of 220° C. Indium metal is used as the calibration standard. Reported values are rounded and should therefore be considered approximate.

FT-IR Spectroscopy

Infrared spectra are acquired on Fourier Transform Infrared Spectrophotometer (FT-IR), a Shimadzu IRPrestige-21 spectrophotometer. It equips with a black-coated heated wire beam source (for KBr method) or air cooled high energy ceramic light source (for diffuse reflection method), and a Germanium coated on potassium bromide (KBr) beamsplitter, and a high sensitivity pyroelectric detector (DLATGS). Each spectrum represents 40 co-added scans collected at a spectral resolution of 4 $cm^{-1}$. For KBr method, the sample and KBr are mixed to prepare the KBr disk and put it on the stage. For diffuse reflection method, a small amount of the sample is put on the plate (6 mm in diameter and 1.5 mm in depth) of the auto-sampler. A background data set is acquired with a blank disk of KBr without samples (KBr method) or a blank sample plate (diffuse reflection method). Wavelength calibration is performed using polystyrene. A Log MR (R=reflectance) spectrum is acquired by taking a ratio of these two data sets against each other (KBr method). Reported values are rounded and should therefore be considered approximate.

Hygroscopicity Study by Dynamic Vapor Sorption Analysis (DVS)

Hygroscopicity study is performed using Surface Measurement Systems DVS-1. The sample is placed on a microbalance in the instrument and the weight change during the sorption/desorption cycle at 25° C. is monitored. One of the sorption/desorption programs consists of a sorption scan from 0 to 95% relative humidity (RH) and a desorption scan from 95 to 10% RH. The other consists of a sorption scan from 40 to 95% RH and desorption scan from 95 to 0% RH, followed by a second sorption scan from 0 to 40% RH. Both programs are carried out at 5% RH increments and the sample is allowed to equilibrate for 360 minutes or until equilibration had been attained at each step. At the end of the DVS experiment the sample is measured by PXRD.

Nuclear Magnetic Resonance (NMR)

NMR data are determined at 270 MHz (JEOL JNM-LA 270 spectrometer) or 300 MHz (JEOL JNM-LA300) using deuterated chloroform (99.8% D) or dimethylsulfoxide (99.9% D) as solvent unless indicated otherwise, relative to tetramethylsilane (TMS) as internal standard in parts per million (ppm); conventional abbreviations used are: s=singlet, d=doublet, t=triplet, q=quartet, m=multiplet, br=broad, etc.

High Performance Liquid Chromatography (HPLC) Measurement

HPLC data are obtained by Waters Alliance 2695 HPLC system with 2996 PDA detector using the following conditions;
Column: Inertsil ODS-3 (3 micrometers, 4.6×150 mm),
Eluent: acetonitrile/10 mM ammonium acetate=32:68,
Detection: UV at 215 nm,
Flow rate: 1 mL/min, and
Column temperature: 40° C.

Data processing is performed with Empower 2 software supplied from Waters Corporation.

Room temperature means 15 to 35° C., but not limited to that as long as the purpose is achieved.

Chemical symbols have their usual meanings; M (mole(s) per liter), L (liter(s)), mL (milliliter(s)), g (gram(s)), mg (milligram(s)), mol (moles), mmol (millimoles), N (normal concentration).

Example 1

Preparation of 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid According to the Conventional Process A mixture of methyl 4-{[4-({[4-(2,2,2-trifluoroethoxy)-1,2-benzisoxazol-3-yl]oxy}methyl)piperidin-1-yl]methyl}-tetrahydro-2H-pyran-4-carboxylate (89 mg, 0.18 mmol, WO2006090224 EXAMPLE 1, Step 5) in tetrahydrofuran (1 mL), methanol (1 mL) and 2N aq. sodium hydroxide (1 mL) is stirred at 70° C. for 17 h. The mixture is neutralized with 2N hydrochloric acid (1 mL) and formed precipitate is filtered. The precipitate is triturated with diethylether to give 50 mg (58%) of the title compound as a white solid.

The symbols "α", "θ", "δ" and "ν" are written as "alpha", "theta", "delta" and "nu", respectively, in this specification.

$^1$H-NMR (DMSO-$d_6$) delta: 7.59 (1H, dd, J=8.1, 8.4 Hz), 7.25 (1H, d, J=8.4 Hz), 6.94 (1H, d, J=8.1 Hz), 4.93 (2H, q, J=8.7 Hz), 4.19 (2H, d, J=5.9 Hz), 3.75-3.62 (2H, m), 3.48-3.30 (2H, m), 2.90-2.74 (2H, m), 2.50 (2H, s), 2.29-2.13 (2H, m), 1.94-1.23 (9H, m).

A signal due to $CO_2H$ is not observed.

MS (ESI) m/z: 473 $(M+H)^+$, 471 $(M-H)^-$.

IR (KBr) nu: 2950, 1617, 1527, 1188, 1113 $cm^{-1}$.

Anal. Calcd for $C_{22}H_{27}N_2O_6F_3$: C, 55.93; H, 5.76; N, 5.93. Found: C, 55.72; H, 5.78; N, 5.80.

Example 2

Preparation of 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form I A mixture of 4-{[4-({[4-(2,2,2-trifluoroethoxy)-1,2-benzisoxazol-3-yl]oxy}methyl)piperidin-1-yl]-methyl}-tetrahydro-2H-pyran-4-carboxylic acid obtained according to the method of EXAMPLE 1 (40 mg, 0.085 mmol) is dissolved in 1,4-dioxane (2 mL) by sonication and vortex mixing, and then frozen in a freezer at −40° C. for several hours. The resultant mixture is dried in vacuo overnight to give a freeze-dried amorphous solid. Ethyl acetate (0.8 mL) is added to the sample and the mixture is heated to 65° C. for dissolution. The resultant solution is gradually cooled to room temperature over 3 days. The precipitate is collected by filtration and dried to afford 27 mg of the white solid. Then a part of the white solid is suspended in ethyl acetate for 1 day at 40° C. and 5 days at room temperature (15-35° C.) to afford a crystalline form of 4-{[4-({[4-(2,2,2-trifluoroethoxy)-1,2-benzisoxazol-3-yl]oxy}methyl)piperidin-1-yl]-methyl}-tetrahydro-2H-pyran-4-carboxylic acid.

The same signals are observed in $^1$H-NMR and MS spectra.

m.p. (DSC onset): 169° C.

Crystallinity by PXRD: Crystal (FIG. 2). Main peaks at 2-theta: 5.9, 9.3, 9.8, 11.9, 13.7, 14.3, 15.0, 17.8, 18.2-19.3, 19.7, 22.6, 23.4-24.5 and 24.9(°). Each peak has a margin of error of +/−0.2(°).

IR (KBr) nu: (FIG. 3). 2948, 1723, 1615, 1535, 1506, 1437, 1383, 1366, 1287, 1262, 1245, 1180, 1164, 1120, 1095, 1059, 1032, 992, 974, 935, 918, 869, 858, 828, 784, 746, 732, 654 and 556 cm$^{-1}$. Each peak has a margin of error of +/−2 cm-1.

IR (diffuse reflection) nu: (FIG. 4). 4389-4383, 3426, 2943-2937, 2120, 1904, 1724, 1614, 1535, 1508, 1437, 1420, 1287, 1261, 1221, 1180, 1121, 1094, 1059, 1022, 991, 974, 957, 934, 918, 868, 827, 783, 746, 731, 654, 638, 615, 588, 554, 542 and 507 cm$^{-1}$. Each peak has a margin of error of +/−2 cm$^{-1}$.

Anal. Calcd for $C_{22}H_{27}N_2O_6F_3$: C, 55.93; H, 5.76; N, 5.93. Found: C, 56.10; H, 5.75; N, 5.99.

Example 3

Preparation of 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form I A slurry of 4-{[4-({[4-(2,2,2-trifluoroethoxy)-1,2-benzisoxazol-3-yl]oxy}methyl)piperidin-1-yl]-methyl}-tetrahydro-2H-pyran-4-carboxylic acid obtained according to the method of EXAMPLE 1 (1.326 kg, 2.807 mol, a white solid) in ethyl acetate (18.564 L) is dissolved at 70° C. The solution is cooled to 64° C. during 35 min and 200 mg of a seed of Polymorph Form I (0.423 mmol) is added to the mixture. The mixture is cooled to 40° C. over 5 h period and stirred at this temperature for 14.5 h. The slurry is gradually cooled to 19° C. during 6 h period and the mixture is stirred at this temperature for 46 h. The formed precipitate is collected by filtration and the filter cake is washed with 2.0 L of ethyl acetate. The filter cake is dried under reduced pressure at 50° C. to afford 1.140 kg of the desired crystalline form of 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid (86%).

Anal. Calcd for $C_{22}H_{27}N_2O_6F_3$: C, 55.93; H, 5.76; N, 5.93. Found: C, 55.76; H, 5.74; N, 5.85.

The other analytical data are same as those in the above EXAMPLE 2.

Example 4

Preparation of 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form II Preparation Method 1)
Polymorph Form I begins to transform to Polymorph Form II at around 110° C.
Preparation Method 2)
4-{[4-({[4-(2,2,2-Trifluoroethoxy)-1,2-benzisoxazol-3-yl]oxy}methyl)piperidin-1-yl]methyl}-tetrahydro-2H-pyran-4-carboxylic acid Polymorph Form I (5 mg) is placed on the temperature-variable sample holder of PXRD, and the temperature of the sample holder is raised to 120° C. and kept for 10 min., then cooled down to room temperature without nitrogen flow to the sample holder to afford Polymorph Form II of 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid. Conversion to the Polymorph Form II is confirmed by in situ monitoring of PXRD spectrum.

m.p. (DSC onset): 167° C.

Crystallinity by PXRD: Crystal (FIG. 5). Main peaks at 2-theta 5.8, 9.7, 10.5, 11.8, 12.4, 13.5, 14.2, 14.6-14.9, 15.4, 17.8, 18.2, 19.9-20.5, 21.2, 21.8, 23.6, 24.1 and 24.6(°) Each peak has a margin of error of +/−0.2(°).

IR (KBr) nu: (FIG. 6). 2950, 1724, 1614, 1534, 1507, 1438, 1383, 1366, 1287, 1262, 1245, 1180, 1164, 1121, 1095, 1059, 1031, 992, 974, 935, 918, 869, 857, 828, 784, 746, 732, 654 and 555 cm$^{-1}$. Each peak has a margin of error of +/−2 cm$^{-1}$.

Example 5

Preparation of 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form III Preparation Method 1)
4-{[4-({[4-(2,2,2-Trifluoroethoxy)-1,2-benzisoxazol-3-yl]oxy}methyl)piperidin-1-yl]methyl}-tetrahydro-2H-pyran-4-carboxylic acid Polymorph Form 1 (100 mg, 0.21 mmol) is laid on a flat dish and stored under 70° C./75% relative humidity condition. After 24 hours, the sample is picked up from the humidity chamber and left an ambient condition to afford 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form III as a white solid. The crystal form is confirmed by PXRD measurement.

Crystallinity by PXRD: Crystal (FIG. 7). Main peaks at 2-theta: 5.5, 10.1, 10.9, 13.9, 15.7, 18.5, 18.9, 20.8, 21.8 and 23.6(°). Each peak has a margin of error of +/−0.2(°).

IR (diffuse reflection) nu: (FIG. 8). 4376-4370, 3525-3519, 3462, 2946-2940, 2127, 1713, 1624, 1537, 1508, 1441, 1368, 1287, 1157, 1121, 1103, 1063, 1034, 1013, 916, 870, 816, 781, 746, 733, 654, 619, 590 and 556 cm$^{-1}$. Each peak has a margin of error of +/−2 cm$^{-1}$.

m.p. (DSC onset): 170° C.

According to Preparation method 1, Polymorph Form I transforms to Polymorph Form III under 60 to 100% relative humidity condition at room temperature 15 to 35° C. or higher.
Preparation Method 2)
A mixture of 4-{[4-({[4-(2,2,2-trifluoroethoxy)-1,2-benzisoxazol-3-yl]oxy}methyl)piperidin-1-yl]-methyl}-tetrahydro-2H-pyran-4-carboxylic acid obtained according to the method of EXAMPLE 3 (50 mg, 0.11 mmol) in 5% (v/v) water—isopropyl alcohol (1.4 mL) is heated to 60° C. and solids are completely dissolved. A seed of Polymorph Form III prepared in Preparation method 1 is added to the mixture during cooling to room temperature. The obtained solids are collected by suction and dried at 40° C. in vacuo to afford 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form III as a white solid.

The same signals as described in WO2006/090224 are observed in $^1$H NMR.

The same signals as described in Preparation method 1 of EXAMPLE 5 are observed in PXRD.

m.p. (DSC onset): 170° C.

According to Preparation method 2, Polymorph Form III is also obtained under the condition of 3 to 5% (v/v) water in isopropyl alcohol or ethanol.

Example 6

Preparation of 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form IV 4-{[4-({[4-(2,2,2-Trifluoroethoxy)-1,2-benzisoxazol-3-yl]oxy}methyl)piperidin-1-yl]methyl}-tetrahydro-2H-pyran-4-carboxylic acid Polymorph Form III begins to transform to Polymorph Form IV at around 90° C. Conversion to the Polymorph Form IV is confirmed by in situ monitoring of PXRD spectrum (variable-temperature PXRD measurement).

Crystallinity by PXRD: Crystal (FIG. 9). Main peaks at 2-theta: 5.6, 9.8, 10.2, 11.3, 13.6, 13.8, 15.7, 17.0, 18.7, 19.3, 21.3 and 22.8(°). Each peak has a margin of error of +/−0.2(°).

Example 7

Preparation of 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form V Preparation Method 1)

4-{[4-({[4-(2,2,2-Trifluoroethoxy)-1,2-benzisoxazol-3-yl]oxy}methyl)piperidin-1-yl]methyl}-tetrahydro-2H-pyran-4-carboxylic acid Polymorph Form I obtained according to the method of EXAMPLE 3 (25 mg, 0.053 mmol) in water (1.25 mL) is stirred for 1 hour at room temperature. The obtained solids are collected by suction and air-dried to afford 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form V as a white solid.

Crystallinity by PXRD: Crystal (FIG. 10). Main peaks at 2-theta 5.2, 10.0, 10.3, 11.6, 15.5, 17.7, 18.6, 19.2, 20.5, 21.7, 22.4 and 24.3(°). Each peak has a margin of error of +/−0.2(°).

IR (diffuse reflection) nu: (FIG. 11). 4381-4375, 4130, 2853, 2760, 1701, 1630, 1618, 1541, 1387, 1281, 1186, 1171, 1157, 1123, 1103, 1069, 1032, 1013, 991, 962, 917, 787, 748, 731, 660, and 650 $cm^{-1}$. Each peak has a margin of error of +/−2 $cm^{-1}$.

m.p. (DSC onset): 169° C.

Preparation Method 2)

4-{[4-({[4-(2,2,2-Trifluoroethoxy)-1,2-benzisoxazol-3-yl]oxy}methyl)piperidin-1-yl]methyl}-tetrahydro-2H-pyran-4-carboxylic acid Polymorph Form I obtained according to the method of EXAMPLE 3 (5 mg, 0.011 mmol) in 10% (v/v) water—tetrahydrofuran (0.15 mL) is heated to 60° C. and solids are completely dissolved. Then the mixture is cooled to room temperature overnight. The obtained solids are collected and air-dried to afford 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form V as a white solid.

The same signals as described in Preparation method 1 of EXAMPLE 7 are observed in PXRD.

According to Preparation method 2, Polymorph Form V is also obtained under the condition of 20% (v/v) or higher water in isopropylalcohol. Similarly, Polymorph Form V is also obtained under the condition of 50% (v/v) or higher water in acetone or acetonitrile and under the condition of 10% (v/v) or higher water in tetrahydrofuran.

Example 8

Preparation of 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form VI 4-{[4-({[4-(2,2,2-Trifluoroethoxy)-1,2-benzisoxazol-3-yl]oxy}methyl)piperidin-1-yl]methyl}-tetrahydro-2H-pyran-4-carboxylic acid Polymorph Form I obtained according to the method of EXAMPLE 3 (100 mg, 0.21 mmol) in 5% (v/v) water—acetone (1.2 mL) is heated to 60° C. and solids are completely dissolved. Then the mixture is cooled to room temperature overnight. The obtained solids are collected and air-dried to afford 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form VI as a white solid.

Crystallinity by PXRD: Crystal (FIG. 12). Main peaks at 2-theta 10.3, 10.6, 11.4, 12.6, 18.8, 19.2, 19.5, 20.2, 21.2 and 21.7(°). Each peak has a margin of error of +/−0.2(°).

IR (diffuse reflection) nu: (FIG. 13). 4378-4372, 3944, 3467-3461, 3306, 2959, 2884, 2835, 1711, 1537, 970, 920, 883, and 785 $cm^{-1}$. Each peak has a margin of error of +/−2 $cm^{-1}$.

m.p. (DSC onset): 170° C.

According to EXAMPLE 8, Polymorph Form VI is also obtained under the condition of 5 to 10% (v/v) water in acetone. Similarly, Polymorph Form VI is also obtained under the condition of 5 to 10% (v/v) water in acetonitrile and under the condition of 5% (v/v) water in tetrahydrofuran.

Example 9

Preparation of 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form III 4-{[4-({[4-(2,2,2-Trifluoroethoxy)-1,2-benzisoxazol-3-yl]oxy}methyl)piperidin-1-yl]methyl}-tetrahydro-2H-pyran-4-carboxylic acid Polymorph Form VI is dried at 40° C. in vacuo for 2 hours to afford 4-{[4-({[4-(2,2,2-trifluoroethoxy)-1,2-benzisoxazol-3-yl]oxy}methyl)piperid in-1-yl]methyl}-tetrahydro-2H-pyran-4-carboxylic acid Polymorph Form III as a white solid.

The same signals as described in Preparation method 1 of EXAMPLE 5 are observed in PXRD.

m.p. (DSC onset): 170° C.

Example 10

[Hygroscopicity Study]

In the hygroscopicity study by dynamic vapor sorption (DVS) analysis, both Polymorph Form III and Polymorph Form V absorb less than 1.2 wt % under 95% relative humidity (RH) at 25° C. On the other hand, the white solid disclosed in the prior art WO2006/090224 and Polymorph Form I absorb 15 wt % or 14 wt % of water under 95% RH at 25° C. The following Table 1 and FIG. 14 show that weight gain % of Polymorph Form III, Polymorph Form V, Polymorph Form I and the white solid disclosed in the prior art WO2006/090224.

TABLE 1

|  | 85% RH | 90% RH | 95% RH |
|---|---|---|---|
| Polymorph Form III | 0.48 | 0.53 | 0.60 |
| Polymorph Form V | 0.74 | 0.85 | 1.1 |
| Polymorph Form I | 0.065 | 0.089 | 14 |
| White solid disclosed in the prior art WO2006/090224 | 0.99 | 5.3 | 15 |

Example 11

[Stability Study]

Solid-state stability study is performed using Nagano Science Constant temperature/humidity control chamber LH-20-11 M, LH-21-11 M, LTL-200D3CJ-14 or LTX-01. The sample is placed in the chamber and exposed under 25° C./60% RH, 40° C./75% RH and/or irradiated with a Xenon lamp. The crystalline form, thermal behavior, purity and/or weight change of the resultant sample after the exposure or irradiation are evaluated by PXRD, TG/DTA or DSC, HPLC, microbalance, respectively.

Polymorph Form I and Polymorph Form III are found to be stable.

In the solid-state stability study after storage at 40° C./75% RH for 1 month, the remaining of Polymorph Form III is 99%, however, the remaining of Polymorph Form I is 98% (Table 2). In addition, less degradation products are found in Polymorph Form III and its purity is higher than Polymorph Form I. The remaining and the purity are determined by HPLC measurement.

TABLE 2

| | Assay | Purity (Area %) | | | | | | |
|---|---|---|---|---|---|---|---|---|
| | | Main peak | Degradant | | | | | |
| | Remaining % | | #1 | #2 | #3 | #4 | #5 | #6 |
| Polymorph Form III | 99 | 99.7 | 0.1 | 0.1 | 0.1 | N.D. | N.D. | <0.1 |
| Polymorph Form I | 98 | 99.4 | 0.2 | 0.1 | 0.1 | 0.1 | <0.1 | N.D. |

Six degradants of 4-{[4-({[4-(2,2,2-Trifluoroethoxy)-1,2-benzisoxazol-3-yl]oxy}methyl)piperidin-1-yl]methyl}-tetrahydro-2H-pyran-4-carboxylic acid are observed. # means each degradant.

N.D. means not detected.

After storage at 40° C./75% RH for 6 months, the remaining of Polymorph Form III is 97% while that of Polymorph Form I is 87% (Table 3). In addition, the purity of Polymorph Form III is 99% and much higher than that of Polymorph Form I, 96%.

TABLE 3

| | Assay | Purity (Area %) | | | | | | |
|---|---|---|---|---|---|---|---|---|
| | | Main peak | Degradant | | | | | |
| | Remaining % | | #1 | #2 | #3 | #4 | #5 | #6 |
| Polymorph Form III | 97 | 99.1 | 0.4 | 0.3 | 0.1 | N.D. | 0.1 | N.D |

TABLE 3-continued

| | Assay | Purity (Area %) | | | | | | |
|---|---|---|---|---|---|---|---|---|
| | | Main peak | Degradant | | | | | |
| | Remaining % | | #1 | #2 | #3 | #4 | #5 | #6 |
| Polymorph Form I | 87 | 95.6 | 1.5 | 0.8 | 1.1 | 0.3 | 0.3 | N.D. |

Six major degradants of 4-{[4-({[4-(2,2,2-Trifluoroethoxy)-1,2-benzisoxazol-3-yl]oxy}methyl)piperidin-1-yl]methyl}-tetrahydro-2H-pyran-4-carboxylic acid are observed. # means each degradant.

N.D. means not detected.

In the solid-state stability study at 70° C./75% RH, Polymorph Form III is chemically and physically stable. The remaining is 100% and 0.01 area % of only one degradation product is found after 3 weeks. On the other hands, Polymorph Form I transforms to Polymorph Form III within 1 day. The remaining and the purity are determined by HPLC measurement.

FIG. 1 shows the PXRD pattern of the reference product described in WO2006/090224. FIG. 2, FIG. 5, FIG. 7, FIG. 9, FIG. 10, and FIG. 12 show the PXRD pattern of Polymorph Form I, Polymorph Form II, Polymorph Form III, Polymorph Form IV, Polymorph Form V and Polymorph Form VI, respectively.

As indicated by the comparison FIG. 1 with FIG. 2, FIG. 5, FIG. 7, FIG. 9, FIG. 10, and FIG. 12, no Polymorph Form disclosed in this patent application corresponds to the reference product described in WO2006/090224, which clearly shows all Polymorph Forms are distinct novel polymorphic forms.

The invention claimed is:

1. 4-{[4-({[4-(2,2,2-Trifluoroethoxy)-1,2-benzisoxazol-3-yl]oxy}methyl)piperidin-1-yl]methyl}-tetrahydro-2H-pyran-4-carboxylic acid Polymorph Form III, which is characterized by a powder X-ray diffraction pattern (PXRD) obtained by irradiation with Cu-Kalpha radiation which includes main peaks at 2-theta 5.5, 10.1, 10.9, 13.9, 15.7, 18.5, 18.9, 20.8, 21.8 and 23.6(°), wherein each peak has a margin of error of +/−0.2(°).

2. The 4-{[4-({[4-(2,2,2-Trifluoroethoxy)-1,2-benzisoxazol-3-yl]oxy}methyl)piperidin-1-yl]methyl}-tetrahydro-2H-pyran-4-carboxylic acid Polymorph Form III according to claim 1, which is further characterized by an infrared (IR) spectrum (diffuse reflection) which shows absorption bands at 4376-4370, 3525-3519, 3462, 2946-2940, 2127, 1713, 1624, 1537, 1508, 1441, 1368, 1287, 1157, 1121, 1103, 1063, 1034, 1013, 916, 870, 816, 781, 746, 733, 654, 619, 590 and 556 cm$^{-1}$, wherein each peak has a margin of error of +/−2 cm$^{-1}$.

3. The 4-{[4-({[4-(2,2,2-Trifluoroethoxy)-1,2-benzisoxazol-3-yl]oxy}methyl)piperidin-1-yl]methyl}-tetrahydro-2H-pyran-4-carboxylic acid Polymorph Form III according to claim 1, which is further characterized by differential scanning calorimetry (DSC) in which it exhibits an endothermic event at 170° C., wherein the temperature has a margin of error of +/−1° C.

4. 4-{[4-({[4-(2,2,2-Trifluoroethoxy)-1,2-benzisoxazol-3-yl]oxy}methyl)piperidin-1-yl]methyl}-tetrahydro-2H-pyran-4-carboxylic acid Polymorph Form IV, which is characterized by a powder X-ray diffraction pattern (PXRD) obtained by irradiation with Cu-Kalpha radiation which includes main peaks at 2-theta 5.6, 9.8, 10.2, 11.3, 13.6, 13.8, 15.7, 17.0, 18.7, 19.3, 21.3 and 22.8(°), wherein each peak has a margin of error of +/−0.2(°).

5. 4-{[4-({[4-(2,2,2-Trifluoroethoxy)-1,2-benzisoxazol-3-yl]oxy}methyl)piperidin-1-yl]methyl}-tetrahydro-2H-pyran-4-carboxylic acid Polymorph Form V, which is characterized by a powder X-ray diffraction pattern (PXRD) obtained by irradiation with Cu-Kalpha radiation which includes main peaks at 2-theta 5.2, 10.0, 10.3, 11.6, 15.5, 17.7, 18.6, 19.2, 20.5, 21.7, 22.4 and 24.3(°), wherein each peak has a margin of error of +/−0.2(°).

6. The 4-{[4-({[4-(2,2,2-Trifluoroethoxy)-1,2-benzisoxazol-3-yl]oxy}methyl)piperidin-1-yl]methyl}-tetrahydro-2H-pyran-4-carboxylic acid Polymorph Form V according to claim 5, which is further characterized by an infrared (IR) spectrum (diffuse reflection) which shows absorption bands at 4381-4375, 4130, 2853, 2760, 1701, 1630, 1618, 1541, 1387, 1281, 1186, 1171, 1157, 1123, 1103, 1069, 1032, 1013, 991, 962, 917, 787, 748, 731, 660, and 650 cm$^{-1}$, wherein each peak has a margin of error of +/−2 cm$^{-1}$.

7. The 4-{[4-({[4-(2,2,2-Trifluoroethoxy)-1,2-benzisoxazol-3-yl]oxy}methyl)piperidin-1-yl]methyl}-tetrahydro-2H-pyran-4-carboxylic acid Polymorph Form V according to claim 5, which is further characterized by differential scanning calorimetry (DSC) in which it exhibits an endothermic event at 169° C., wherein the temperature has a margin of error of +/−1° C.

8. 4-{[4-({[4-(2,2,2-Trifluoroethoxy)-1,2-benzisoxazol-3-yl]oxy}methyl)piperidin-1-yl]methyl}-tetrahydro-2H-pyran-4-carboxylic acid Polymorph Form VI, which is characterized by a powder X-ray diffraction pattern (PXRD) obtained by irradiation with Cu-Kalpha radiation which includes main peaks at 2-theta 10.3, 10.6, 11.4, 12.6, 18.8, 19.2, 19.5, 20.2, 21.2 and 21.7(°), wherein each peak has a margin of error of +/−0.2(°).

9. The 4-{[4-({[4-(2,2,2-Trifluoroethoxy)-1,2-benzisoxazol-3-yl]oxy}methyl)piperidin-1-yl]methyl}-tetrahydro-2H-pyran-4-carboxylic acid Polymorph Form VI according to claim 8, which is further characterized by an infrared (IR) spectrum (diffuse reflection) which shows absorption bands at 4378-4372, 3944, 3467-3461, 3306, 2959, 2884, 2835, 1711, 1537, 970, 920, 883, and 785 cm$^{-1}$, wherein each peak has a margin of error of +/−2 cm$^{-1}$.

10. The 4-{[4-({[4-(2,2,2-Trifluoroethoxy)-1,2-benzisoxazol-3-yl]oxy}methyl)piperidin-1-yl]methyl}-tetrahydro-2H-pyran-4-carboxylic acid Polymorph Form VI according to claim 8, which is further characterized by differential scanning calorimetry (DSC) in which it exhibits an endothermic event at 170° C., wherein the temperature has a margin of error of +/−1° C.

11. A pharmaceutical composition comprising the 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form III according to claim 1, and at least one pharmaceutically acceptable excipient.

12. A process for preparing the 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form III according to claim 1, comprising a step of exposing 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form I to a relative humidity condition in the range of 60 to 100% at room temperature or higher.

13. A process for preparing the 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form III according to claim 1, comprising a step of exposing 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form I to 3 to 5% (v/v) water in alcohol.

14. A process for preparing the 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form IV according to claim 4, comprising a step of placing 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form III in an atmosphere of 90 to 115° C.

15. A process for preparing the 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form V according to claim 5, comprising a step of exposing 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form I under a condition to form Polymorph Form V without forming any other crystalline forms in a mixture of water and an organic solvent.

16. A process for preparing the 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form VI according to claim 8, comprising a step of exposing 4-{[4-({[4-(2,2,2-trifluoroethoxy)-1,2-benzisoxazol-3-yl]oxy}methyl)piperidin-1-yl]methyl}-tetrahydro-2H-pyran-4-carboxylic acid Polymorph Form I under a condition to form Polymorph Form VI without forming any other crystalline forms in a mixture of water and an organic solvent.

17. The 4-{[4-({[4-(2,2,2-Trifluoroethoxy)-1,2-benzisoxazol-3-yl]oxy}methyl)piperidin-1-yl]methyl}-tetrahydro-2H-pyran-4-carboxylic acid Polymorph Form III according to claim 1, wherein the Form III has a purity of at least 90% by weight.

18. The 4-{[4-({[4-(2,2,2-Trifluoroethoxy)-1,2-benzisoxazol-3-yl]oxy}methyl)piperidin-1-yl]methyl}-tetrahydro-2H-pyran-4-carboxylic acid Polymorph Form III according to claim 2, wherein the Form III has a purity of at least 90% by weight.

* * * * *